(12) United States Patent
Limem et al.

(10) Patent No.: US 10,507,020 B2
(45) Date of Patent: Dec. 17, 2019

(54) IMPLANTABLE FASTENER FOR ATTACHMENT OF A MEDICAL DEVICE TO TISSUE

(71) Applicant: Tepha, Inc., Lexington, MA (US)

(72) Inventors: Skander Limem, Melrose, MA (US); Bruce Van Natta, Westfield, IN (US); Kevin Cristadoro, Edina, MN (US)

(73) Assignee: Tepha, Inc., Lexington, MA (US)

( * ) Notice: Subject to any disclaimer, the term of this patent is extended or adjusted under 35 U.S.C. 154(b) by 157 days.

(21) Appl. No.: 15/292,592

(22) Filed: Oct. 13, 2016

(65) Prior Publication Data

US 2017/0105724 A1  Apr. 20, 2017

Related U.S. Application Data

(60) Provisional application No. 62/241,841, filed on Oct. 15, 2015.

(51) Int. Cl.
*A61B 17/04* (2006.01)
*A61F 2/12* (2006.01)
(Continued)

(52) U.S. Cl.
CPC ........ *A61B 17/064* (2013.01); *A61B 17/0401* (2013.01); *A61B 17/809* (2013.01);
(Continued)

(58) Field of Classification Search
CPC ... A61B 17/80–8095; F16B 2015/0069; F16B 15/003
See application file for complete search history.

(56) References Cited

U.S. PATENT DOCUMENTS 1,806,522 A * 5/1931 De Gruyter ............... E04B 1/49
411/458
3,172,171 A * 3/1965 Knight ..................... E04B 1/49
411/458
(Continued)

FOREIGN PATENT DOCUMENTS

EP        1532942      5/2005
WO       01067944      9/2001
(Continued)

OTHER PUBLICATIONS

Williams, et al., "Poly-4-hydroxybutyrate (P4HB): a new generation of resorbable medical devices for tissue repair and regeneration" Biomed. Tech. 58(5):439-52 (2013).
(Continued)

*Primary Examiner* — Zade Coley
(74) *Attorney, Agent, or Firm* — Pabst Patent Group LLP

(57) ABSTRACT

Implantable fasteners that can be repositioned after implantation, and implants including these repositionable implantable fasteners, have been developed. The fasteners are designed to fixate medical devices and other implantable components in the body, and can be adjusted after initial fixation in tissue to reposition the implanted medical device. The fasteners include a plurality of tissue retainers emanating from a supportive backing, wherein the tissue retainers can swivel from the plane of the supportive backing to engage tissue. The fasteners are fixated in tissue by movement in a first direction, and can be removed when pulled in a direction opposite to the first direction. The fasteners may be attached to medical devices before or after implantation. In one embodiment, the implant is a mastopexy device in the form of a mesh and the repositionable fastener.

43 Claims, 12 Drawing Sheets

(51) Int. Cl.
  *A61B 17/064*  (2006.01)
  *A61B 17/80*  (2006.01)
  *A61F 2/00*  (2006.01)
  *A61B 17/56*  (2006.01)
  *A61B 17/00*  (2006.01)

(52) U.S. Cl.
  CPC .............. *A61F 2/0063* (2013.01); *A61F 2/12* (2013.01); *A61B 2017/00004* (2013.01); *A61B 2017/00792* (2013.01); *A61B 2017/00796* (2013.01); *A61B 2017/00889* (2013.01); *A61B 2017/00898* (2013.01); *A61B 2017/0437* (2013.01); *A61B 2017/0464* (2013.01); *A61B 2017/0641* (2013.01); *A61B 2017/561* (2013.01); *A61F 2002/0068* (2013.01); *A61F 2220/0016* (2013.01)

(56) References Cited

U.S. PATENT DOCUMENTS

| | | | | |
|---|---|---|---|---|
| 6,712,830 | B2* | 3/2004 | Esplin | A61B 17/0401 606/152 |
| 6,893,452 | B2* | 5/2005 | Jacobs | A61B 17/064 606/215 |
| 7,172,615 | B2* | 2/2007 | Morriss | A61B 90/02 606/215 |
| 7,510,566 | B2* | 3/2009 | Jacobs | A61B 17/064 606/215 |
| 2001/0051815 | A1* | 12/2001 | Esplin | A61B 17/0401 606/232 |
| 2003/0065360 | A1* | 4/2003 | Jacobs | A61B 17/064 606/216 |
| 2003/0105464 | A1* | 6/2003 | Schreurs | A61B 17/809 606/300 |
| 2004/0234576 | A1* | 11/2004 | Martin | B29C 48/022 424/426 |
| 2004/0254609 | A1* | 12/2004 | Esplin | A61B 17/0401 606/232 |
| 2008/0027273 | A1* | 1/2008 | Gutterman | A61F 2/0045 600/37 |
| 2008/0200993 | A1* | 8/2008 | Henderson | A61F 2/0059 623/23.74 |
| 2010/0331612 | A1* | 12/2010 | Lashinski | A61B 17/0401 600/37 |
| 2012/0203253 | A1* | 8/2012 | Kubiak | A61B 17/1146 606/151 |
| 2016/0151167 | A1* | 6/2016 | Jo | A61F 2/4455 623/17.16 |

FOREIGN PATENT DOCUMENTS

| | | |
|---|---|---|
| WO | 2008088716 | 7/2008 |
| WO | 2012122215 | 9/2012 |
| WO | 2015006737 | 1/2015 |

OTHER PUBLICATIONS

International Search Report and Written Opinion for corresponding PCT application PCT/US2016/056861 dated Dec. 21, 2016.

* cited by examiner

IMPLANTABLE FASTENER FOR ATTACHMENT OF A MEDICAL DEVICE TO TISSUE

CROSS-REFERENCE TO RELATED APPLICATIONS

This application claims benefit of U.S. Provisional Application No. 62/241,841, filed Oct. 15, 2015, the contents of which are incorporated by reference herein in their entirety.

FIELD OF THE INVENTION

The present invention generally relates to the field of surgery, and more particularly, the invention relates to implants with one or more repositionable fasteners that facilitate attachment of the implant to tissue. The fastener has a plurality of tissue retainers that can swivel from a supportive backing and engage tissue. Medical devices may be fixated to tissue by attachment to the fastener, and engagement of the fastener in tissue. The fastener may be a part of the implant. The design of the fastener allows the medical device to be repositioned if necessary after initial implantation.

BACKGROUND OF THE INVENTION

Numerous plastic surgery procedures are performed each year to restore or correct the form or function of the body. Many of these procedures seek to restore a youthful appearance, or even to enhance one's existing appearance. Natural factors, such as aging and gravity, contribute to the loss of the youthful appearance. For example, skin laxity, loss of muscle tone, and attenuation of ligaments can result in ptosis (drooping) of the breast. Plastic surgeons have developed a plethora of surgical techniques to correct the ptosis of different anatomical structures that occurs with aging. These techniques vary in the type of incision, direction of incision, plane of dissection, amount of dissection, extent of repositioning of tissue, the use of different types of sutures, different suturing techniques, and different fixation techniques. Almost all of them rely on the use of the pre-existing skin envelope as the support system for the newly lifted tissue. These approaches almost invariably result in recurrent ptosis, since the surgeon is merely relying on the aging and sagging surrounding tissues that have already failed to provide the necessary support to maintain a normal appearance. At most, these techniques only slow recurrent ptosis by creating internal scars that provide limited reinforcement.

Several surgeons have attempted to reinforce their lift procedures using surgical meshes in mastopexy and breast reconstruction procedures. Some of these techniques have also incorporated the use of various reinforcing materials similar to those used in hernia repair, such as flat polymeric meshes, allografts, xenografts and autografts. For example, in 1981, Johnson described the use of MARLEX® (crystalline polypropylene) mesh to convert the support of breast tissue after mastopexy from a cutaneous origin to a skeletal origin by attaching the mesh to the area of the second rib, (Johnson, *Aesth. Plast. Surg.* 5:77-84 (1981)). The flat MARLEX® mesh is a permanent mesh made from polypropylene, and was implanted to provide two slings in each breast that supported the breast tissue. The MARLEX mesh was secured to the fascia with Mersilene sutures.

More recently, WO2015/006737 to Felix and WO2012/122215 to Moses have disclosed the use of resorbable meshes for mastopexy with properties that allow the meshes to resorb and be replaced with host tissue without recurrent ptosis. Furthermore these procedures can, if desired, be performed in a minimally invasive manner.

While the use of mesh in mastopexy has significant advantages for the patient, correct and precise placement of the mesh by the surgeon is required for a successful outcome. For example, the surgeon not only needs to sculpt the breast into the desired shape, but also needs to make sure that each breast is positioned at the same height. The correct positioning of the breasts can be particularly difficult because surgeons generally work with the patient lying horizontal on the operating table. As a consequence, surgeons will frequently need to make adjustments to the position of the mesh in order to make sure the breasts are correctly positioned. During this process, the surgeon will often sit the patient up on the operating table in order to identify adjustments that need to be made to the position of the mesh so that the breasts are positioned at the same height or so that the desired breast shape is obtained. Since the mesh is usually fixated to the patient's tissue using either sutures, screws, or anchors, the process of optimizing breast shape and position can be difficult because it may require, for example, sutures to be cut and placed in a different position or for screws and anchors to be removed and/or replaced. A fixation technique that would allow the surgeon to make quick adjustments to the position of the mesh during a mastopexy procedure without needing to cut and replace sutures, or remove and replace screws or bone anchors, would be very desirable. Such a technique would also be desirable in other surgical procedures, particularly where it is often necessary to make adjustments to the position of medical devices, or where fixation is difficult and requires additional time.

A fixation technique that allows a surgeon to make adjustments without removal and replacement of sutures, screws, or bone anchors would also be highly desirable in minimally invasive procedures, and in open procedures where there is restricted access to the fixation site. For example, it would be particularly desirable to have a fixation technique that allows mesh to be easily fixated in a lateral position during a mesh-assisted mastopexy procedure. In these procedures, it is often difficult for the surgeon to anchor the mesh in the lateral position because: (i) access is restricted; (ii) little tissue is available for fixation; and (iii) nerves in the lateral position, which should not be trapped, make fixation challenging. Surgeons have attempted to use barbed sutures and staples for fixation when access to a fixation site is restricted, however, these fixation systems cannot be adjusted once implanted. It would therefore be desirable to identify a method to fixate medical devices, such as mesh in a mesh-assisted mastopexy procedure, wherein the device can be more easily fixated at a restricted position and re-positioned as needed.

It is therefore an object of the invention to provide an implantable fastener for attachment of a medical device to tissue, wherein the fastener can be fixated in a first position, removed from that position, and repositioned in a second position different from the first position.

It is another object of the invention to provide an implantable fastener for attachment of a medical device to tissue, wherein the fastener can be fixed in a first position by movement in a first direction, and removed when pulled in a direction opposite to the first direction.

It is still another object of the invention to provide an implant comprising a fastener attached to a medical device, wherein the location of the fastener may be adjusted after initial implantation from a first position, and moved to a second position different from the first position by removing the fastener from the first position and implanting it at the second position.

It is yet another object of the invention to provide an implant for mastopexy, wherein the implant comprises a mesh and a repositionable fastener, and wherein the fastener can be fixated to tissue.

It is still a further object of the invention to provide implants and implantable fasteners that comprise a plurality of tissue retainers emanating from a supportive backing, wherein the tissue retainers can swivel from the plane of the supportive backing to engage tissue.

SUMMARY OF THE INVENTION

Implantable fasteners that can be repositioned after implantation, and implants including these repositionable implantable fasteners, have been developed. The fasteners are designed to fixate medical devices in the body, can be used to apply tension to a connected medical device, and can be adjusted after initial fixation in tissue to reposition the implanted medical device. The fasteners include a supportive backing, a gripping feature for gripping tissue following implantation and in optional embodiments, an attachment feature. The attachment feature may or may not be integral to the fastener, medical device or other implantable component.

In a preferred embodiment, the gripping feature is a plurality of tissue retainers emanating from a supportive backing. The tissue retainers can swivel from the plane of the supportive backing to engage tissue. In one embodiment, the implant is a mastopexy device and can include one, two, three, four, five or six repositionable fasteners.

Also disclosed is a method of is a method of fixating a medical device in tissue. The method includes attaching the device to one or more repositionable fasteners via the attachment feature of the fastener and fixing the device in tissue via the gripping feature of the fastener. The repositionable fasteners are fixated in tissue by movement in a first direction, and can be removed when pulled in a direction opposite to the first direction. The fasteners may be attached to medical devices before or after implantation.

DETAILED DESCRIPTION OF THE INVENTION

Figure 1:
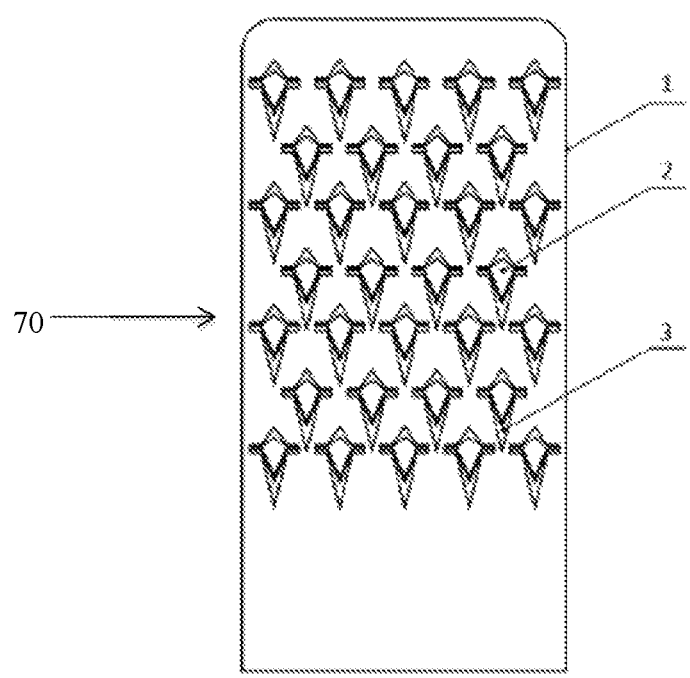
FIG. 1 shows a repositionable implantable fastener (70) with a supportive backing (1), tissue retainer (2), and the tip of a tissue retainer (3), that can penetrate tissue. The repositionable implantable fastener (70) shown in this figure includes a total of 32 tissue retainers emanating from the supportive backing (1).

Ideally, it would be preferable to make adjustments to the positions of certain implants after initial implantation in the body without the need to remove and replace sutures, staples, screws or bone anchors. For example, a surgeon may implant a mesh to lift a breast in a mastopexy procedure, but then decide to reposition the mesh to provide a better outcome. This will typically require the removal of sutures, staples, screws or bone anchors that are holding the mesh in place, movement of the mesh to a new position, and fixation at the new position with new sutures, staples, screws or bone anchors. The use of implants with repositionable fasteners could however permit the surgeon to make adjustments to the location of the implant without the need to remove and replace fixation devices such as sutures, staples, screws and bone anchors. Such repositionable fasteners could allow initial implantation and subsequent adjustments to the position of an implant to be made without the use of sutures, staples, screws and bone anchors. An implant with a repositionable fastener that fixates tissue using tissue retainers emanating from the supportive backing of the fastener could provide a means to fixate an implant without the use of sutures, staples, screws and bone anchors, and also provide a means to relocate the position of the implant without the need to remove and replace sutures, staples, screws and bone anchors. Such an implant could be relocated after initial implantation by pulling the repositionable fastener in a direction opposite to the direction used to implant the fastener retainers in tissue, moving the implant to the desired position, and re-implanting the fastener by piercing the tissue with the retainers to fixate the implant at the relocated position.

Furthermore, it would be desirable to provide the surgeon with a means to easily fixate an implant deployed in a minimally invasive procedure or in a procedure where there is restricted access to the attachment/fixation site. And the option to be able to relocate the position of the implant without removing and replacing sutures, staples, screws, and bone anchors. Implants with repositionable fasteners could be deployed through small access sites, or in small spaces and hard to reach areas. After locating the implant in the desired position, the repositionable fastener could be used to fix the implant in position by using retainers emanating from the fastener to pierce tissue and hold the implant in place. There would be no need to insert, for example, sutures, screws or bone anchors. Such fastener devices could help to reduce the need to use sutures in hard to reach areas, such as in serratus anterior-breast applications and ligamentous sacrospinous fixation for vaginal vault applications, and improve the precision of placement of fixation. This would also be desirable given that it would reduce operating times, for example, by eliminating suturing times. If desired, the implant could also be repositioned as described above.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" is used herein to refer to therapeutic, prophylactic or diagnostic agents, preferably agents that promote healing and the regeneration of host tissue, and also therapeutic agents that prevent, inhibit or eliminate infection agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Copolymers of poly-4-hydroxybutyrate" as generally used herein means any polymer containing 4-hydroxybutyrate with one or more different hydroxy acid units.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Swivel" as used herein means to turn around an axis.

"Retainer" as generally used herein means an element that is adapted to penetrate tissue and resist movement in any direction other than the direction in which the retainer was deployed into tissue. Examples of retainers, include, but are not limited to, barbs, hooks, projections, darts, extensions, bulges, anchors, protuberances, spurs, cogs, bumps, points, arrows, spikes, and spurs. The retainers may be pointed, jagged, tapered, serrated, sharp edged, wedge-shaped, thorn-shaped, shield-shaped, V-shaped, W-shaped, and multi-tipped.

"Tissue" as used herein includes both soft and hard tissues.

II. Repositionable Fasteners and Implants with Repositionable Fasteners

Repositionable fasteners have been developed that can be implanted in the body in a first position, removed from that position, and re-implanted in a second position different from the first position. The repositionable fasteners also eliminate the need to use sutures, staples, screws, bone anchors or other similar devices to fixate medical devices in the body. The repositionable fasteners are used to attach medical devices to tissue, and are preferably attached to medical devices to form implants. For example, the repositionable fasteners may be incorporated into a surgical mesh device in order to fixate the surgical mesh device in vivo. The implants so formed preferably have a pyrogen level of less than 20 endotoxin units per device.

A. Repositionable Fasteners

The fasteners include a supportive backing, a gripping feature for gripping tissue following implantation and in optional embodiments, an attachment feature. In some embodiments, the supportive backing is porous. The repositionable fasteners have been designed to support the mechanical forces acting on them. The repositionable fastener must have sufficient strength to fixate a medical device to tissue, and be strong enough to support a mechanical load that may, for example, also include a load placed on the fastener by an additional implant, such as a breast implant.

The fixation strength of the fastener will depend upon variables such as the type of tissue, number of tissue retainers emanating from the supportive backing, the size of the fastener, the dimensions and shapes of the tissue retainers, the angles of penetration of the tissue retainers in tissue, the materials used to make the fastener, and the forces applied to the retainer by any attached medical device. Preferably the fastener is strong enough to hold a force when anchored in tissue (a pullout force) between 10 gf (gram force) and 35 kgf (kilogram force), more preferably between 100 gf and 25 kgf, and even more preferably between 1 kgf and 10 kgf.

In an embodiment, the supportive backing has a tensile strength between 1 MPa and 10 GPa, more preferably between 50 MPa and 5 GPa, and even more preferably between 100 MPa and 3 GPa. The elongation to break of the supportive backing may be between 1 and 1,200%, but is more preferably between 1 and 100%, and even more preferably between 1 and 50%. However, it is desirable that the fastener or supportive backing of the fastener cannot elongate more than 100%, more preferably more than 50% and even more preferably more than 30% when implanted. In a particularly preferred embodiment, the implanted fastener should elongate between 0% and 30% when subjected to mechanical forces in vivo.

Preferably, the repositionable fastener is made from a resorbable material. When the repositionable fastener is made with an absorbable material, the fastener can be designed to allow a steady transition of mechanical forces to regenerated host tissues such that the regenerated host tissues can support those mechanical forces once the absorbable material has been resorbed. Design of the fastener includes selection of the absorbable material, its form, degree of orientation, molecular weight, surface area and porosity.

The fasteners and implants can be coated, derivatized, or modified with other agents, including therapeutic, prophylactic and/or diagnostic agents.

Figure 4:
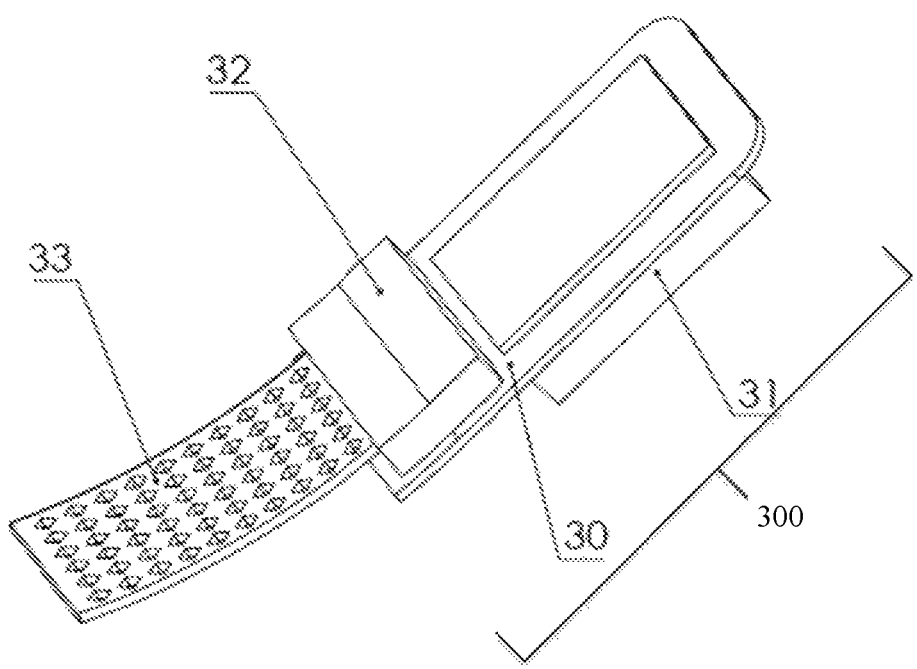
FIG. 4 is a diagram showing an implantable repositionable fastener (300) (which includes a supportive backing (30), and a gripping feature (31)), and an attachment feature (32). The implantable repositionable faster (300) is attached to a medical device (33) via the attachment feature (32), which in optional embodiments, can be an integral part of the repositionable fastener (300).

FIG. 4 shows a diagram of an implantable repositionable fastener (300) which includes a supportive backing (30) connected to a medical device (33) (for example, a mesh for soft tissue support) using an attachment feature (32). The implantable repositionable fastener (300) includes a gripping feature (31) projecting from the plane of the supportive backing (30). The gripping feature (31) is a tissue retainer.

(i). Supportive Backing

The fastener includes a supportive backing with a plurality of tissue retainers emanating from the supportive backing. The supportive backing is generally made from a film, sheet, thermoform, foam, molded object, or laminate, but it can also be a mesh, net or lattice and is preferably, flexible.

In general, the thickness of the supportive backing will range between 100 µm and 5 mm, and more preferably, between 250 µm and 5 mm within a specific fastener. Thus, films and sheets for preparation of the fasteners preferably have a thickness between 100 µm and 5 mm, and more preferably between 0.25 mm and 1 mm.

In an embodiment, the tensile modulus of the supportive backing of the fastener is between 1 MPa and 6 GPa, more preferably between 50 MPa and 4 GPa, and even more preferably between 70 MPa and 2 GPa.

Figure 2A:
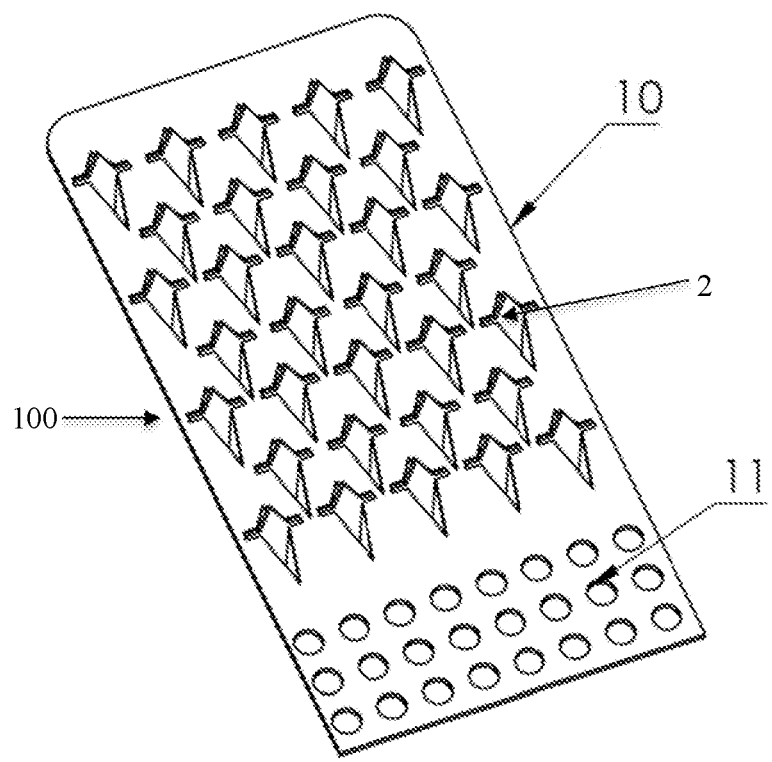
FIG. 2A shows an implantable fastener (100) with tissue retainers that swivel (2) and a supportive backing (10), which includes pores (11).
Figure 2B:
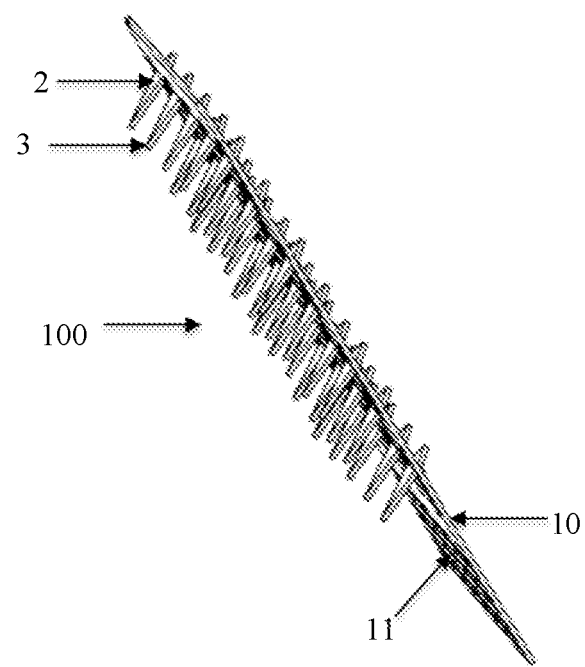
FIG. 2B is a side view of the repositionable implantable fastener (100) showing the tissue retainers (2), swiveled at an angle from the plane of the supporting backing (10), which includes pores (11).

In some embodiments, the supportive backing may be porous. The pore diameters can be between 50 µm and 5 mm, and more preferably between 100 µm and 1 mm. One example of a porous supportive backing is shown in FIG. 2. This figure shows a supportive backing (10) with pores/perforations (11) in the supportive backing. Adding pores to the supportive backing or increasing its total surface area can be advantageous particularly when the supportive backing is designed to degrade in vivo. Adding pores to a degradable supporting backing may increase the degradation rate of the supportive backing, and also potentially increase cell in-growth. Cell in-growth can also help to increase the fixation of the supportive backing to tissue, and therefore increase the fixation strength of the fastener to tissue. The pores contemplated in these embodiments are distinct and different from the holes shown in FIG. 7B (64a-c) which are designed/configured to receive locking pins (66a-c), and which will be occupied (and thus closed) when the locking pins engage the holes in the closed position (FIG. 7B)

The supportive backing may include folds, waves or grooves to assist in holding the supportive backing against tissue. Areas of the supportive backing may also function like suction caps to help hold the supportive backing against the tissue. The cross-section of the supportive backing may also be varied to promote flexibility in specific regions, and minimize local stress. Preferably the supportive backing has rounded edges, smooth edges, or edges that minimize tissue irritation.

The degree of flexibility of the supportive backing is determined by: (i) the material used to construct the backing, (ii) the shape of the backing, (3) the dimensions of the backing, and (4) the number and type of tissue retainers that can swivel from the supportive backing. The degree of flexibility required for the supportive backing will depend upon where the fastener is placed in vivo, its function, and the properties of the tissue that it will be fastened to. For example, a more flexible fastener would be required in a curved part of the body, or where there is more motion. A more flexible fastener would also be desirable in locations where the patient might feel a stiffer fastener. A more flexible fastener is also more desirable in curved parts of the body where bending of the supportive backing could otherwise decrease the number of tissue retainers that can penetrate the tissue. The flexibility of the supportive backing will also depend upon its thickness and porosity, and possibly also, on its width and length.

(ii) Tissue Retainers

The supportive backing includes a plurality of tissue retainers. The shape of the tissue retainers may be varied, for example, based on the application, location of the implant, and the type of tissue that will be penetrated by the retainers. At minimum, the tissue retainers must be able to penetrate tissue. The shape of the tissue retainers may be, for example, one or more of the following: barbs, hooks, projections, darts, extensions, bulges, anchors, protuberances, spurs, curved, bumps, points, arrows, spikes, spurs, pointed, jagged, tapered, serrated, sharp edge shaped, wedged-shaped, thorn-shaped, shield-shaped, V-shaped, W-shaped, cogs, and multi-tip.

The number of tissue retainers emanating from the supportive backing can range between 2 and 1,000, and is more preferably between 4 and 100. The density, distribution, length, and orientation of the retainers emanating from the supportive backing may be modified depending on the type of tissue and device being fixated. The retainers may be positioned in an ordered manner, random manner, spiral manner, patterned manner or staggered manner. Preferably, the number of retainers and arrangement of the retainers is selected so that tension on the tissue engaged by the fastener is uniformly distributed over a large contact area, for example, when compared to the tension placed on a suture and the area occupied by a suture. In a particularly preferred embodiment, the retainers are all oriented in (or face) the same direction. This allows the fastener to be fixed in a first position by movement in a first direction, and removed when pulled in a direction opposite to the first direction. In general, the distance between the tissue retainers will range from 50 µm and 2.5 cm, and more preferably between 0.5 mm and 5 mm.

The tissue retainers may be designed to engage tissue at an angle between 1° and 90° from the plane of the supportive backing, preferably at an angle between 5° and 60°, and more preferably at an angle between 15° and 45°. The thickness of the tissue retainers will depend upon the type of tissue and medical device to be fixated. The retainers may typically have a thickness between 100 µm and 5 mm. The thickness of the retainers may also vary between 100 µm and 5 mm in a fastener. In general, the length of the tissue retainers, measured from the plane of the supportive backing to the tip of the retainer that pierces tissue, is between 0.01 mm and 10 mm, and more preferably is between 0.25 mm and 5 mm. In one embodiment the size of the repositionable fastener allows the surgeon to deliver an implant or fastener through a small incision.

The tissue retainers of the repositionable fastener are designed to penetrate tissue to a depth between 0.01 mm and 10 mm, more preferably between 1 mm and 6 mm, and even more preferably between 2 mm and 5 mm.

In one embodiment, the tissue retainers can swivel from the supportive backing, penetrate and engage tissue. In another embodiment, the tissue retainers do not swivel from the plane of the supportive backing, however, the retainers are all oriented in the same direction such that the fastener can be removed from tissue when pulled in a direction opposite from the direction used to implant the fastener.

FIG. 1 shows a picture of an implantable fastener (70) wherein 25 tissue retainers (2) have been cut in a supportive backing (1) to make an implantable fastener with tissue retainers that can swivel from the plane of the supportive backing to engage tissue. The tips of the tissue retainers (3) are sharp, and can penetrate tissue.

The ability of the tissue retainers to swivel can be varied by adjusting the size of the axle that the tissue retainer swivels around. The angle of the tissue retainers relative to the supportive backing can also be set by heat setting the fastener. In one preferred embodiment, the angle of the tissue retainers is fixed, for example by heat setting so that the tissue retainers do not lie in the plane of the supportive backing. In another embodiment, the tissue retainers have a spring action such that they tend to align in the plane of the supportive backing or within a 30° angle of the plane of the supportive backing unless catching on tissue. The spring action helps to facilitate the removal of the fastener from tissue (since the retainers spring back into or towards the plane of the supportive backing) and subsequent redeployment (when the retainers can swivel again and be caught on new tissue).

Figure 5A:
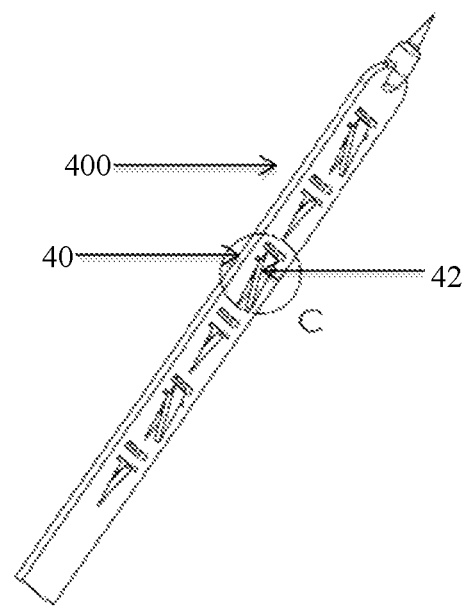
FIG. 5A shows a section (400) of a repositionable fastener, including a supportive backing (40) and tissue retainer (42).
Figure 5B:
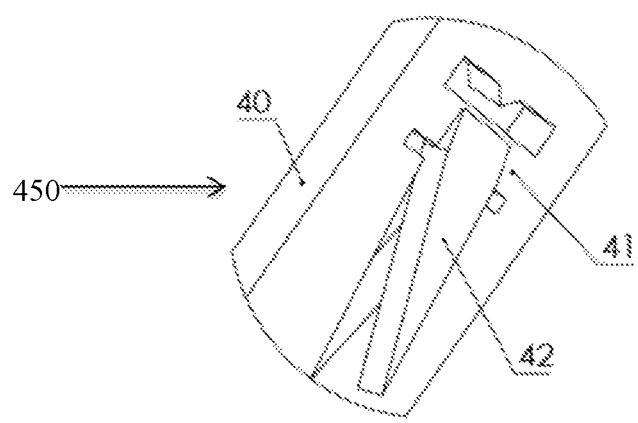
FIG. 5B is an enlarged view (450) of a section (represented as "C" in FIG. 5A), of the repositionable faster section (400) showing the supportive backing (40) and the tissue retainer (42) (with its lance feature) which can swivel about its axle (41) from the plane of the supportive backing (40).

FIG. 5 is a diagram showing a section of supportive backing (40) of a fastener, and a tissue retainer (42) that can swivel about its axle (41) from the plane of the supportive backing. The resistance of a tissue retainer to swiveling about its axle can be adjusted by varying the dimensions of the axle, for example, by changing the thickness of the supportive backing, the width, or the diameter of the axle. Tissue retainers may be cut in the supportive backing using any suitable technique for cutting the backing, including, but not limited to: mechanical cutting, machining, laser cutting, stamping, or punching. Alternatively, molding can be used to form the supportive backing and swivel retainers.

(iii) Attachment Features

Suitable attachment features include, but are not limited to, a locking device, clasp, buckle, latch, clip, glue or pin.

Figure 6A:
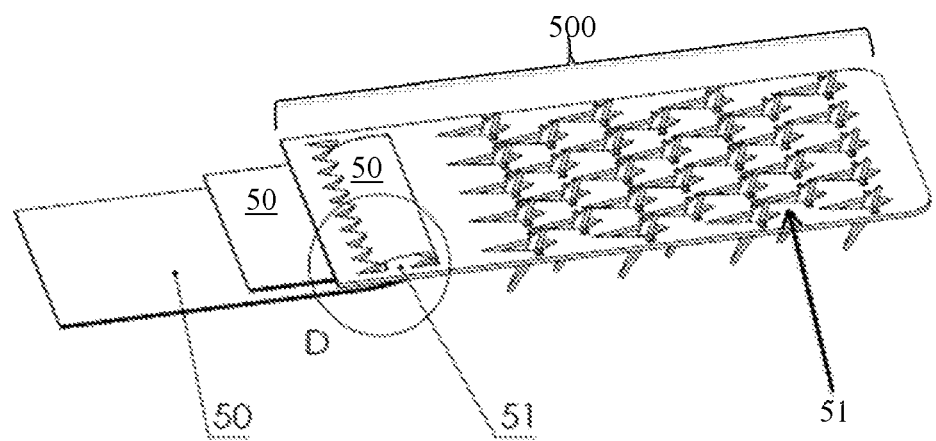
FIG. 6A shows a mesh tab (50) of a mastopexy device buckled to the supportive backing (51) of a repositionable fastener (500). An adjustable buckle formed by locking teeth (54a, 54b, etc.) connects the mesh tab (50) of the mastopexy device to the repositionable fastener (500).
Figure 6B:
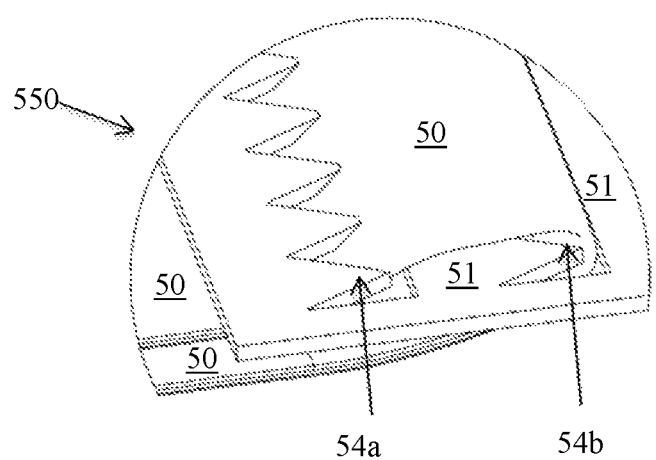
FIG. 6B is an enlarged view (550) of a section (represented as "D" in FIG. 6A) of the adjustable buckle feature, showing the locking teeth (54a, 54b).

An example of a fastener with a buckle to attach a medical device to the fastener is shown in FIGS. 6A and 6B. FIG. 6A shows how a mesh tab (50) of a mastopexy device can be buckled to the repositionable fastener (500) using an adjustable buckle (51). The adjustable buckle has locking teeth (54a, 54b, etc.) and can connect the mesh tab (50) of the mastopexy device to the repositionable fastener (500). It will be apparent from FIG. 6A, that the buckle (51) provides an additional means to vary the tension on the medical device, and that this may also be possible when a clasp, such as that shown in FIGS. 7A and 7B, is used to connect the medical device to the fastener.

Figure 7A:
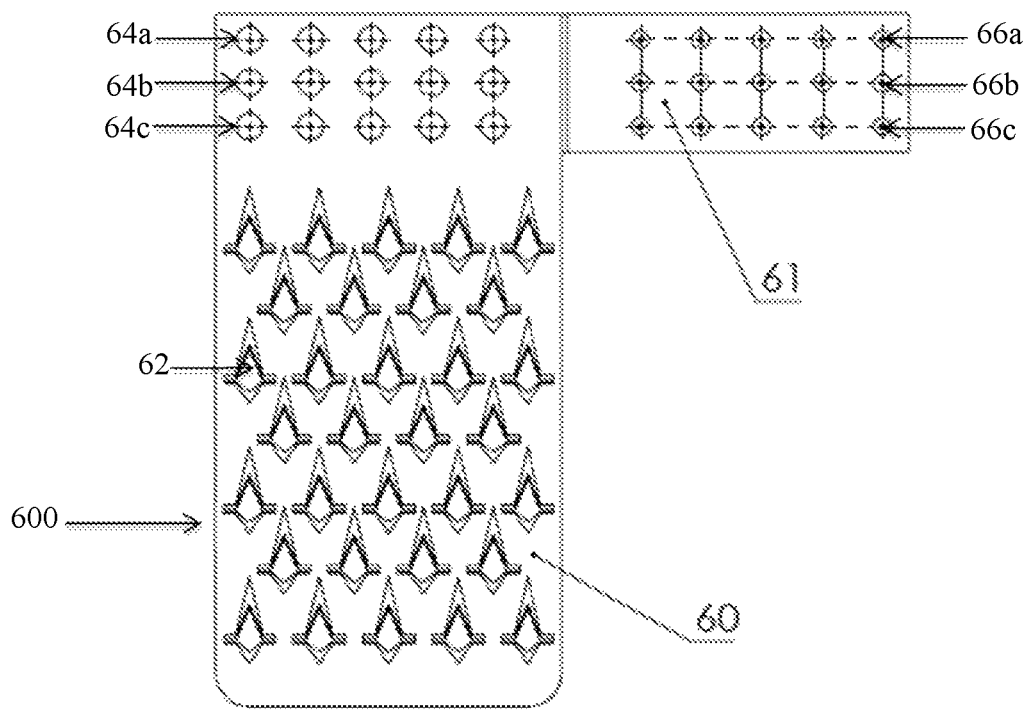
FIG. 7A shows a front view repositionable fastener (600). The repositionable fastener includes a supportive backing (60) and an attachment feature (herein, a clasp (61)) in the open position that can be used to attach a medical device to the fastener (600) and tissue retainers (62).
Figure 7B:
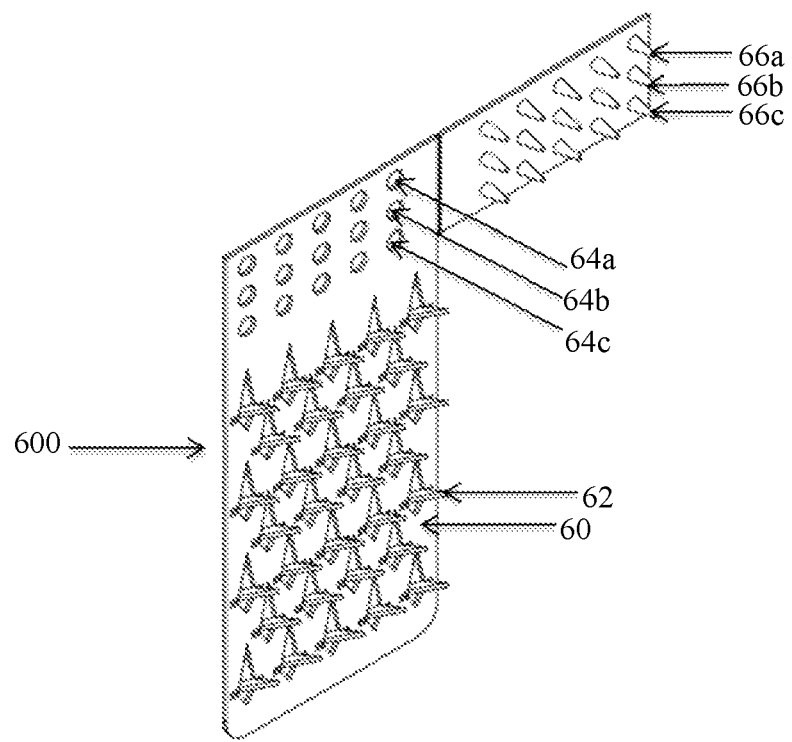
FIG. 7B shows a dimetric projection view the repositionable fastener (600), showing the clasp (61), which includes locking pins (66a, 66b, 66c, etc.), configured to mate into locking holes (64a, 64b, 64c, etc.) on the backing (60) of the repositionable fastener (600).
Figure 7C:
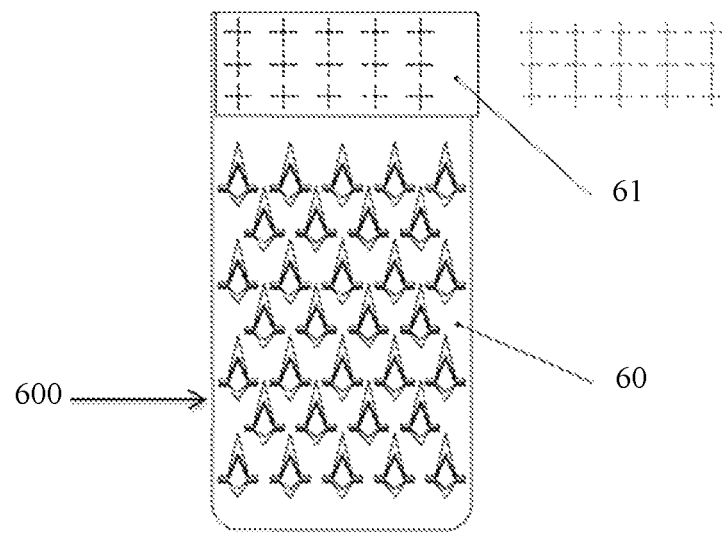
FIG. 7C shows the repositionable fastener (60) with the clasp (61) in the closed position.
Figure 7D:
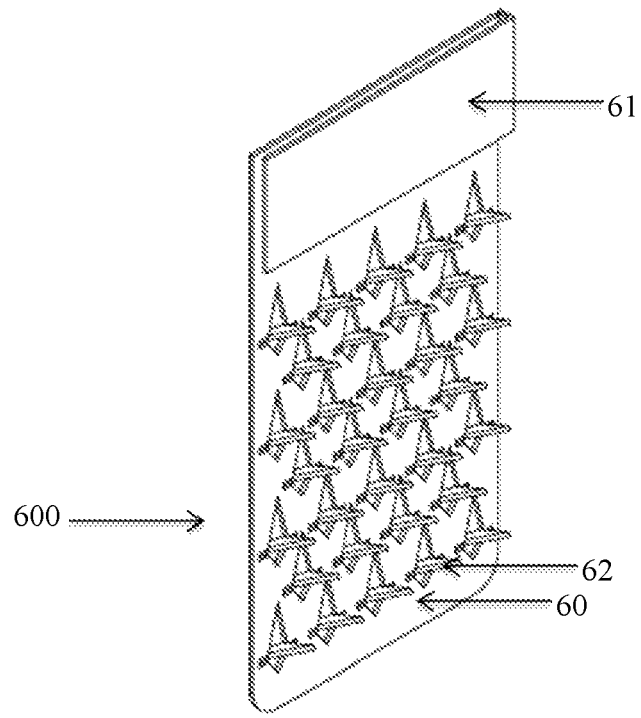
FIG. 7D shows a dimetric projection view of the repositionable fastener (60) with the clasp (61) in the closed position.

An example of a fastener with a clasp to attach a medical device to the fastener is shown in FIGS. 7A-7D. FIG. 7A shows a front view repositionable fastener (600), which includes a supportive backing (60) and an attachment feature (herein, a clasp (61)) in the open position that can be used to attach a medical device to the fastener (600) and tissue retainers (62). FIG. 7B shows a dimetric projection view of the repositionable fastener (600), showing the clasp (61), which includes locking pins (66a, 66b, 66c, etc.), configured to mate into pores (64a, 64b, 64c, etc.) on the backing (60) of the repositionable fastener (600). FIG. 7C shows the repositionable fastener (60) with the clasp (61) in the closed position. FIG. 7D shows a dimetric projection view of the repositionable fastener (60) with the clasp (61) in the closed position.

B. Medical Devices

Medical devices that can be used with the repositionable fasteners include, but are not limited to: monofilament mesh, multifilament mesh, patch, monofilament fiber, multifilament fiber, braid, ligature, knitted mesh, woven mesh, knitted tubes, wound healing device, bandage, wound dressing, skin substitute, hemostat, organ salvage device, dural substitute, dural patch, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, bladder repair device, sphincter muscle repair device, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, cardiovascular patch, vascular closure device, intracardiac septal defect repair device, PFO (patent foramen ovale) closure device, left atrial appendage (LAA) closure device, pericardial patch, myocardial regeneration device, periodontal mesh, anastomosis device, plastic surgery device, breast lift device, mastopexy device, breast reconstruction device, breast augmentation device, breast reduction device, device for breast reconstruction following mastectomy, facial reconstructive device, forehead lift device, brow lift device, eyelid lift device, face lift device, rhytidectomy device, rhinoplasty device, device for malar augmentation, otoplasty device, neck lift device, mentoplasty device, and cosmetic repair device. A particularly preferred medical device that can be attached to the repositionable fastener is a surgical mesh, more preferably a monofilament mesh, and even more preferably a monofilament mesh made from poly-4-hydroxybutyrate. Another particularly preferred medical device that can be attached to the repositionable fastener is a mastopexy device.

The medical devices described above may be attached to one, two, three, four, five, six or more repositionable fasteners to form an implant, for example, using a locking device, clasp, buckle, latch, clip, pin, stitching, glue or by fusing the fastener to the device.

C. Materials for Preparing Repositionable Fasteners and Implants with Repositionable Fasteners Any biocompatible materials may be used to make the repositionable fastener, including permanent materials such as metals, alloys, ceramics, and non-degradable polymers. Examples of suitable metals and alloys include stainless steel, tantalum, titanium, cobalt-chromium, iron, zirconium, manganese, and magnesium alloys, and Nitinol. Examples of suitable non-degradable polymers include polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, and poly(ethylene oxide).

In a preferred embodiment, the repositionable fastener is made from an absorbable material, such as an absorbable polymer or degradable metal (such as degradable iron or magnesium based alloys). The fastener and the entire implant may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone and copolymers thereof, including random copolymers and block copolymers thereof. Preferably the polymer or copolymer will be substantially resorbed within a 1 to 24 month timeframe, and retain some residual strength for at least 2 weeks-2 months, and more preferably at least 3-6 months.

Blends of polymers, preferably absorbable polymers, can also be used to prepare the fasteners and implants. Particularly preferred blends of absorbable polymers are prepared from absorbable polymers including, but not limited to, polymers of glycolic acid, lactic acid, 1,4-dioxanone, trimethylene carbonate, 3-hydroxybutyric acid, 4-hydroxybutyrate, ε-caprolactone or copolymers thereof.

In a particularly preferred embodiment, poly-4-hydroxybutyrate (P4HB) or a copolymer thereof is used to make the repositionable fastener, and may also be used to make an implant including the fastener attached to a medical device (i.e. the medical device is also made from P4HB or copolymer thereof). Copolymers include P4HB with another hydroxyacid, such as 3-hydroxybutyrate, and P4HB with glycolic acid or lactic acid monomer. Poly-4-hydroxybutyrate (P4HB, TephaFLEX® biomaterial) is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for prolonged strength retention.

D. Additives

Certain additives may be incorporated into the absorbable polymer, copolymer or blends thereof. Preferably, these additives are incorporated during a compounding process to produce pellets that can be subsequently melt-processed. For example, pellets may be extruded into films or sheets suitable for making the supportive backing of the fastener. In another embodiment, these additives may be incorporated using a solution-based process, for example, layers of film may be cast from solutions of the polymer and one or more additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to improve the mechanical properties of the supportive backing of the fastener and the tissue retainers. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the fasteners and implants include, but are lot limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In yet another embodiment, the additives are ceramics, more preferably bioceramics, and even more preferably resorbable bioceramics. Examples of resorbable bioceramics that can be incorporated into the compositions for making the fasteners and implants include tricalcium phosphate ($\alpha$ and $\beta$ forms of tricalcium phosphate (TCP))—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be used. Bioactive glasses include bioactive glasses composed of $SiO_2$, $Na_2O$, $CaO$ and $P_2O_5$ in specific proportions.

E. Therapeutic, Prophylactic and Diagnostic Agents

The fasteners and implants can be coated, derivatized, or modified with other agents, including bioactive agents, in order to improve wettability, water contact angle, cell attachment, tissue in-growth, tissue maturation or to deliver active agents. Or these agents may be incorporated into the body of the fasteners and implants for such purposes.

The fasteners and implants disclosed herein can contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The fasteners and implants can incorporate wetting agents designed to improve the wettability of the surfaces of the fastener and implant structures to allow fluids to be easily adsorbed onto the fastener or implant surfaces, and to promote cell attachment and or modify the water contact angle of the fastener or implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifyers.

The fasteners and implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, polysaccharides such as hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

Diagnostic agents that can be incorporated into the fasteners and implants include contrast agents, radiopaque markers, or radioactive substances.

The implants may also contain allograft material and xenograft materials. In yet another preferred embodiment, the implants may incorporate systems for the controlled release of the therapeutic or prophylactic agents.

III. Methods of Manufacturing Fasteners

A variety of methods can be used to manufacture the fasteners and implants. Suitable methods include, but are not limited to melt extrusion, melt extrusion using an inflation method, solvent casting, compression molding, injection molding and laminating.

In one embodiment, the fastener is prepared from a film or sheet, and the film or sheet is used to prepare the supportive backing and the tissue retainers of the fastener. The film or sheet may be unoriented, or oriented in one or more directions. In a preferred embodiment, the film or sheet is made from poly-4-hydroxybutyrate or copolymer thereof by melt extrusion preferably using a T-die extrusion method or an inflation method. However, the film or sheet may also be prepared by solvent casting or compression molding.

The films and sheets for preparation of the fasteners preferably have a thickness between 100 µm and 5 mm, and more preferably between 0.25 mm and 1 mm. In another embodiment, the films and sheets have a tensile strength between 1 MPa and 10 GPa, preferably between 50 MPa and 5 GPa, and even more preferably between 100 MPa and 3 GPa. In yet another embodiment, the films and sheets have a tensile modulus between 1 MPa and 6 GPa, more preferably between 50 MPa and 4 GPa, and even more preferably between 70 MPa and 2 GPa. In a further embodiment, the films and sheets have an elongation to break between 1 and 1,200%, more preferably between 1 and 100%, and even more preferably between 1 and 50%.

The films and sheets can be porous. Porous films and sheets can be prepared either directly, for example, by techniques such as particulate leaching or phase separation, or they can be prepared by forming pores in a second step in the films and sheets. For example, porous films and sheets can be prepared by mechanical or laser drilling, punching, or any similar method to create pores in a suitable film or sheet. Pores may also be introduced into the fastener by mechanical or laser drilling after the fastener has been formed. Preferably the pores in the films and sheets that are used to prepare the fastener are between 50 µm and 5 mm, and more preferably between 100 µm and 1 mm.

A. Methods of Forming films or Sheets for Repositionable Fasteners (i) Melt extrusion The P4HB film or sheet may be formed by melt-extrusion, using barrel and T-die temperatures between 80 and 250° C., and more preferably 100 to 220° C. After extrusion from the T-die, the extrudate is preferably cast over a chilled moving surface, preferably one or more rotating cylindrical cast rollers with surface temperatures maintained preferably at 5-20° C. After this step, the solidified film or sheet may be collected, for example, using a winder. The thickness of the film or sheet can be varied by changing one or more of the following: the gap of the T-die slit, polymer flow rate, cooling air pressure and temperature and cast roll speed.

(ii) Melt Extrusion-Inflation Method

P4HB films and sheets suitable for making the fastener may also be prepared by extrusion using an inflation method wherein an inflation molding circular die is used instead of a T-die to extrude cylindrical film or sheet. After exiting the circular die, the molten cylindrical film or sheet is cooled by blowing it up using cold air blown from the central portion of the circular die. Once the polymer has solidified, the film or sheet may be collected using a take-up machine. Films or sheets of P4HB or copolymer thereof with different thicknesses can be produced by changing the gap of the inflation die slit, as well as altering the polymer flow rate, cooling air pressure, temperature of the air, and the take-up speed.

(iii) Solvent Casting

Films and sheets of a P4HB homopolymer, copolymer or blend thereof, can be prepared by solvent casting. In a preferred embodiment, a solution of P4HB can be prepared by dissolving the polymer, copolymer or blend in a solvent at a concentration preferably of 10-15 wt/vol %, or at a concentration such that the solution has a viscosity of 400 to 7,400 cP. Suitable solvents include tetrahydrofuran, 1,4-dioxane, acetone, chloroform, and methylene chloride. The polymer solution is pumped through a slot die onto a moving web such as, for example, an aluminum foil. The distance traveled by the moving web before being taken up on a collection roller is adjusted to ensure evaporation of the solvent, and one or more air-drying zones, preferably with elevated temperatures, may be used to speed up solvent evaporation. In one embodiment, the slot die has a width of 150 mm and a 400 µm die gap, and the web speed is 0.5 m/min with the web traveling 5 m before the film is collected on a final roll. The pump speed, die gap and width, polymer concentration, and web speed may all be varied to produce films and sheets of P4HB homopolymer, copolymer or blends thereof of the desired thickness and widths.

(iv) Compression Molding

Suitable films and sheets for preparing the fastener may also be prepared by compression molding, preferably of P4HB or copolymer or blend thereof. In an embodiment, compositions of P4HB homopolymer, copolymer or blend thereof may be pressed into films and sheets using a Carver hydraulic press. In a preferred embodiment, compositions of P4HB powder, granules or pellets can be pressed into films and sheets by heating the platens of the press to 115° C., and pressing the composition between two sheets of Mylar using metal spacers. After pressing, the film or sheet is removed from the press, allowed to cool and solidify, and removed from the Mylar backing material. The thickness of the metal spacers may be adjusted in order to produce films and sheets of the desired thickness.

(v). Injection Molding

Figure 11:
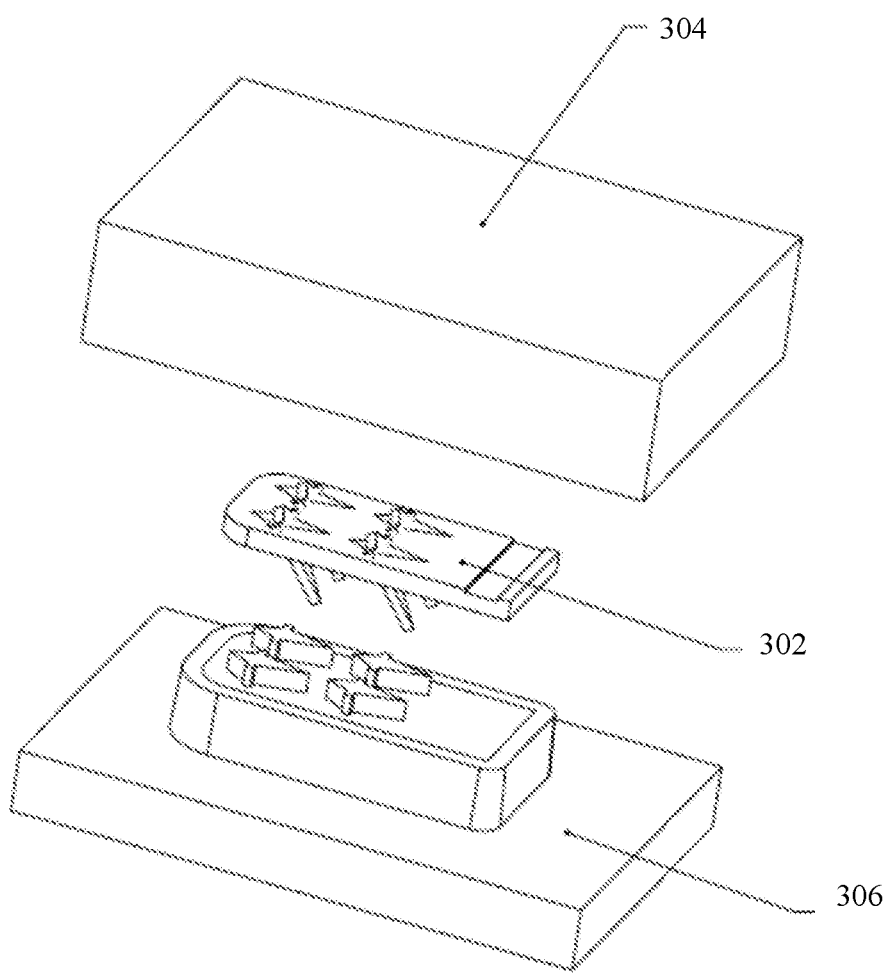
FIG. 11 is a diagram illustrating an equipment setup for producing a fastener with swivel anchors by injection molding, showing a top half (cavity) of the injection mold (304), a molded repositionable fastener (302), and a bottom half (cavity) of the injection mold (306).

In an alternative embodiment, the repositionable fasteners can be produced using a molding technique, such as injection molding (see, for example, FIG. 11). FIG. 11 shows a top half (cavity) of the injection mold (304), a molded repositionable fastener (302), and a bottom half (cavity) of the injection mold (306). A negative mold can be prepared that can be used in the molding process to produce the desired fastener in a single molding step. This technique is generally preferred when repositionable fasteners with tissue retainers that do not swivel. When injection molding is used to produce the fasteners, the supportive backing and tissue retainers may be formed in one step from a suitable mold. If desired the mold can be designed so that the fastener is produced with pores, or these can be inserted after molding in a second step. A preferred material for injection molding a repositionable fastener is poly-4-hydroxybutyrate or copolymer thereof.

(vi) Orienting Films or Sheets

If desired, the P4HB films or sheets produced as described herein may be oriented by any suitable method, including but not limited to roll stretching or use of a tenter frame. The film or sheet can be stretched at ambient temperature, or at a temperature between ambient temperature and 150° C., preferably with stretch ratios between 0.25 and 15. In a preferred embodiment, the film or sheet is stretched at a temperature between 40 and 90° C. The stretching may be monoaxial for forming a monoaxially oriented film, or consecutive or simultaneous biaxial stretching for forming a biaxially oriented film or sheet. When the film or sheet is stretched, the tensile strength at break in the direction in which the film or sheet is stretched is increased. Suitable equipment to orient the films and sheets includes the Bruckner Karo IV stretching machine.

In another embodiment, the oriented films or sheets can be heat set or annealed. The films or sheets may be heat set by restraining the films or sheets at the desired stretch dimensions, and heating to a temperature of less than 60° C., and more preferably 35° C. to 55° C. In a preferred embodiment, the films or sheets are heated in a water bath while maintaining the film or sheet in a stretch condition.

In addition to the method described above, the films or sheets may also be derived by co-extrusion of polymers, copolymers or blends.

B. Processing films or sheets into repositionable Fasteners

Figure 8:
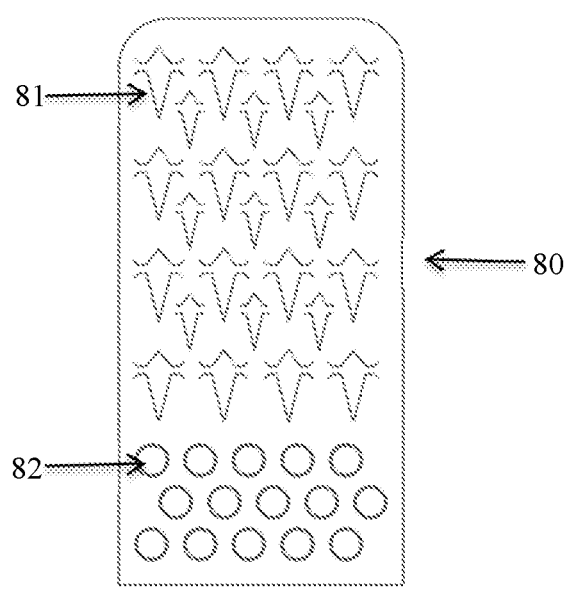
FIG. 8 is a diagram showing the design of retainers (81) and pores (82) to be laser cut from a sheet or film (80) in order to produce a repositionable fastener.

The repositionable fasteners can be fabricated from the films and sheets disclosed herein by cutting the films and sheets by mechanical or thermal means. In an embodiment, the films and sheets are cut to form the tissue retainers and the supportive backing. In a preferred embodiment, the films and sheets are cut to form the tissue retainers and the supportive backing using a predefined design. FIG. 8 is an example of a predefined design showing both retainers (81) and pores (82) to be cut from a sheet or film (80) in order to produce a repositionable fastener. The design shown in FIG. 8 will yield a fastener with 30 tissue retainers, and 24 pores. However, the design shown in FIG. 8 may be varied in order to change the number of tissue retainers, their dimensions, shapes, positions, and sizes.

In an embodiment, the number of tissue retainers cut in the film or sheet is between 2 and 1,000, and more preferably between 4 and 100. The distance between the tissue retainers cut in the film or sheet is preferably between 50 µm and 2.5 cm, and more preferably between 0.5 and 5 mm. The length of the tissue retainers cut in the sheet or film, measured from the plane of the supportive backing to the end of the tip that pierces tissue, is preferably between 0.01 mm and 10 mm, and more preferably between 0.25 mm and 5 mm. The predefined design can also be varied in order to produce tissue retainers with different shapes. For example, the design shown in FIG. 8 may be changed in order to produce the following tissue retainer shapes: barbs, hooks, projections, darts, extensions, bulges, anchors, protuberances, spurs, curved, bumps, points, arrows, spikes, spurs, pointed, jagged, tapered, serrated, sharp edge shaped, wedged-shaped, thorn-shaped, shield-shaped, V-shaped, W-shaped, cogs, and multi-tipped retainers.

Tissue retainers may be cut in the films and sheets using any suitable technique for cutting the films and sheets, including, but not limited to: mechanical cutting, machining, laser cutting, stamping, die cutting, or punching. These methods may also be used to cut the shape of the fastener from the film or sheet (i.e. the overall dimensions of the supportive backing). In a preferred embodiment, the films and sheets are cut with a laser according to a predefined design. In a particularly preferred embodiment, the films and sheets are cut with a $CO_2$ laser, excimer laser or femtosecond laser. In a particularly preferred embodiment, the retainers are designed and cut from the film or sheet using a laser in a manner so that they will be able to swivel to engage tissue upon implantation once released from the supportive backing.

Other methods, such as stamping or die cutting, may also be used instead of laser cutting to produce the tissue retainers from the film or sheet, however, in this instance mechanical pressure is applied to a custom made stamp or die placed above the film or sheet so that the stamp or die cuts through the film or sheet. The custom made stamp or die incorporates the desired predefined design for the tissue retainers.

Figure 10:
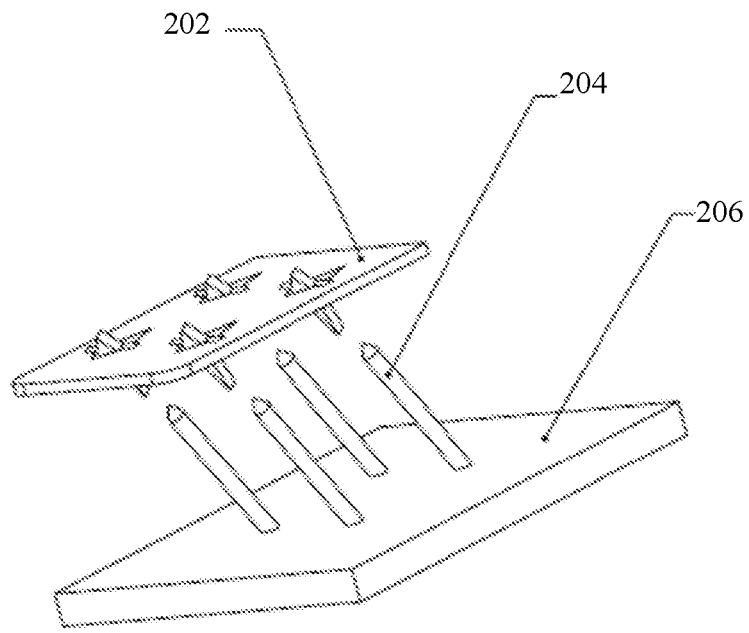
FIG. 10 is a diagram showing the equipment setup used to set the angle of the tissue anchors emanating from the supportive backing of the fastener. The set up includes a base plate (206), orientation needles (204) set at the desired angle from the plate (206) and a supportive backing with cut anchors (202).

After cutting the film or sheet with, for example, a laser or die to form the tissue retainers in the supportive backing, as well as the perimeter of the repositionable fastener, excess film or sheet extending beyond the perimeter of the fastener may be removed, and the tissue retainers can be released from the supportive backing (i.e. from the cut film or sheet). In one embodiment, the tissue retainers are released from the cut film or sheet by placing the cut film or sheet onto an angle plate consisting of a metal base with orientation pins. An example of an angle plate with orientation pins is shown in FIG. 10. The set up includes a base plate (206), orientation needles (204) set at the desired angle from the plate (206) and a supportive backing with cut anchors (202). All the pins of the angle plate are press-fit to the metal base plate at a constant angle. This orientation angle may be varied between 1° and 90° from the base of the plate, but is more preferably 15° to 60°, and even more preferably 30° to 45°. The number of pins used per plate is set to equal the number of tissue retainers cut in the film or sheet, and the pins are aligned on the base plate so that they line up directly with the top half of the tissue retainers as shown in FIG. 10. Once the tissue retainers cut in the film or sheet have been aligned with the orientation pins, the tissue retainers are released from the cut film or sheet by driving the pins through the top half of the tissue retainers. As the pins pierce through the cut film or sheet, the tissue anchors separate from the film or sheet and rotate so that they protrude from the film or sheet at the same angle of the pins relative to the metal base plate. This process forms a supportive backing with protruding tissue retainers that can swivel. In another embodiment, the tissue retainers may be released from the supportive backing manually.

The tissue retainers may be heat set after the retainers have been deployed from the cut film or sheet by the orientation pins. In one embodiment, the tissue retainers are heat set by immersing the assembly of the fastener on the angle plate with the orientation pins in a hot water bath, and then transferring the assembly to a cold water bath for quenching. In a particularly preferred embodiment, a fastener made from poly-4-hydroxybutyrate is heat set in a hot water bath for 10-20 seconds at 57° C., and then quenched in a cold water bath at ≤18° C. for a minimum of 10 minutes. The assembly is then removed from the cold water bath, and allowed to dry. This procedure allows the tissue retainers to be set at any desired angle.

IV. Methods of Manufacturing Implants with the Fasteners

The fasteners described herein may be attached to a medical device or other implantable component to form an implant. The implants are preferably formed prior to implantation, but could also be formed during a surgical procedure by implanting the medical device (or other implantable component) and then fixing the fastener to the medical device and attaching it to tissue.

The repositionable fastener may be attached to the medical device to form an implant by any suitable attachment feature or means, including, but not limited to, the following: locking device, clasp, buckle, latch, clip, pin, stitching, glue or fusing of the fastener to the medical device.

These attachment features may or may not be integral to the fastener, medical device or other implantable component. An example of a fastener with a clasp to attach a medical device or other implantable component to the fastener is shown in FIGS. 7A and 7B. FIG. 7A shows a repositionable fastener (60) with a clasp (61) in the open position that can be used to attach a medical device or other implantable component to the fastener. FIG. 7D shows a repositionable fastener (600) with a clasp (61) in the closed position that can be used to attach a medical device to the fastener. The clasp may incorporate, for example, pins that can be driven through the medical device to secure the device to the fastener when the clasp is closed. For example, pins may be used to penetrate the pores of a mesh that is attached to a repositionable fastener using a clasp.

An example of a fastener with a buckle to attach a medical device to the fastener is shown in FIG. 6. FIG. 6 shows how a mesh tab of a mastopexy device can be buckled to the repositionable fastener (52) using an adjustable buckle (51). The adjustable buckle has locking teeth (in this example two parallel saw edge slots) and can connect the mesh tab of the mastopexy device to the repositionable fastener. It will be apparent from FIG. 6, that the buckle (51) provides an additional means to vary the tension on the medical device, and that this may also be possible when a clasp, such as that shown in FIGS. 7A and 7B, is used to connect the medical device to the fastener. In an embodiment, the attachment feature is made from a resorbable polymer, copolymer or blend. In a preferred embodiment, the attachment feature includes a polymer, copolymer or blend made from one or more of the following monomers: glycolic acid, glycolide, lactic acid, lactide, 1,4-dioxanone, trimethylene carbonate, 3-hydroxybutyric acid, 4-hydroxybutyric acid, or ε-caprolactone. In a particularly preferred embodiment, the attachment feature includes poly-4-hydroxybutyrate or copolymer thereof.

Figure 3A:
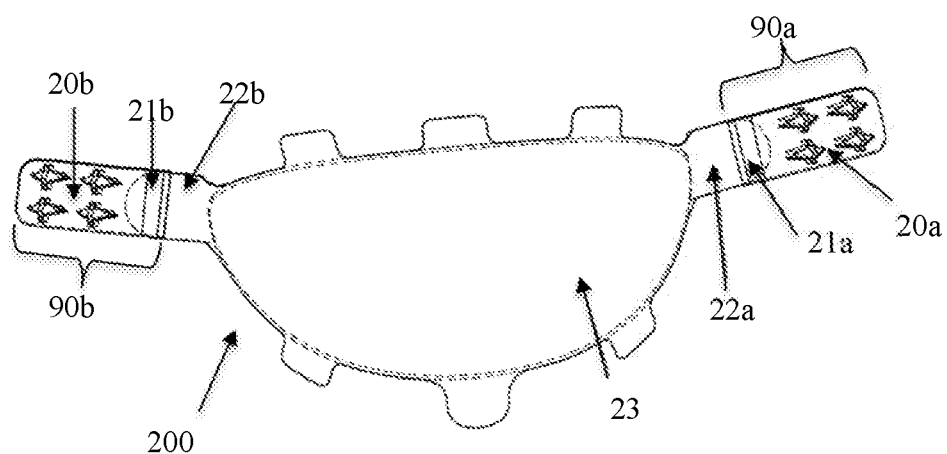
FIG. 3A shows a mastopexy implant (200) showing an implantable repositionable fasteners (90a and 90b) with supportive backings (20a and 20b) attached by fusion at locations (21a and 21b) to mesh tabs (22a, 22b) of a mastopexy device (23).
Figure 3B:
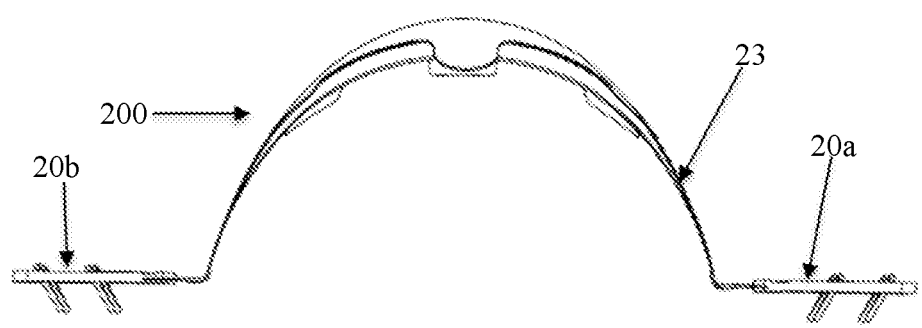
FIG. 3B is a side view of the implant (200), shown in FIG. 3A.
Figure 12:
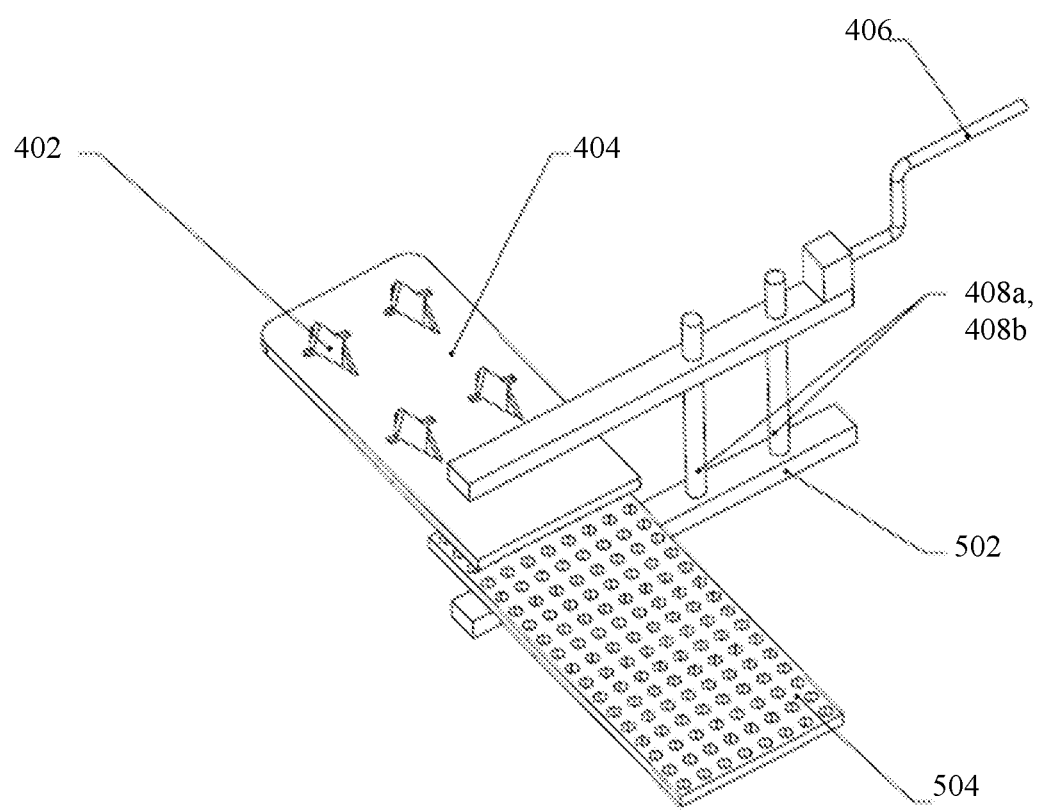
FIG. 12 is a diagram illustrating an exemplary equipment setup for attaching a fastener to a mesh by fusion (heat welding), showing oriented swivel anchors (402), a supportive backing (404), an electric or fluid supply depending on sealer type (406), alignment pins (408a, 408b) to apply uniform pressure during sealing, a heat setter (502), set at 57-60° C. (for processing P4HB, for example), and a substrate (504) to the supportive backing (404) onto.

In another embodiment, the repositionable fastener may be attached to the medical device or implantable component to form an implant by directly coupling the fastener to the medical device or implantable component. This may be achieved, for example, by methods including, but not limited to, the following: stitching, gluing or fusing of the fastener to the medical device or implantable component. In one particularly preferred embodiment, the repositionable fastener can be attached to the medical device or implantable component by fusion. FIG. 3 shows an example of repositionable fasteners (90a, 90b) (that have been fused to a three-dimensional mesh (mastopexy device) (23) for use in a mastopexy procedure. In this example, both the mesh (23) and the repositionable fasteners (90a, 90b) are made from poly-4-hydroxybutyrate, and each tab (22a, 22b) of the mastopexy mesh device (23) have been fused at a location (21a, 21b) to the repositionable fastener (90a, 90b). Fusion at location (21a, 21b) can be achieved by placing the mesh tabs (22a, 22b) and the repositionable fastener (90a, 90b) together between two heated plates, heating while applying pressure, and then quenching. For example, heating at 55-65° C. for 2-3 minutes while applying a pressure of 5-10 psi followed by quenching in a cold water bath for a minimum of 10 minutes can be used to fuse the mesh tab to the repositionable fastener. A suitable apparatus for achieving this fusion is shown in FIG. 12. In a preferred embodiment, the fastener is stitched to the medical device or implantable component using a resorbable fiber, and even more preferably using a fiber including poly-4-hydroxybutyrate or copolymer thereof.

Examples of medical devices and other implantable components that can be attached to the repositionable fastener, include, but are not limited to: monofilament mesh, multifilament mesh, patch, monofilament fiber, multifilament fiber, braid, flat braid, circular braid, ligature, suture, knitted mesh, woven mesh, knitted tubes, wound healing device, bandage, wound dressing, skin substitute, hemostat, organ salvage device, device for soft tissue reinforcement, dural substitute, dural patch, hernia repair device, hernia mesh, hernia plug, device to surgically alter or tighten the lower esophageal sphincter (LES) in order to prevent backflow in the treatment of gastro esophageal reflux disease (GERD), device for temporary wound or tissue support, tissue scaffold, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of stress incontinence, bladder repair device, sphincter muscle repair device, ligament repair device, ligament augmentation device, ligament graft, anterior cruciate ligament repair device, tendon repair device, devices for Achilles tendon repair as adjunct reinforcement, tendon graft, tendon augmentation device, rotator cuff repair device, device for Tommy John's repair/ulnar ligament graft reinforcement, device for reinforcement in knee procedures including the reinforcement of anterior, posterior and medial cruciate ligaments, meniscus repair device, meniscus regeneration device, articular cartilage repair device, cardiovascular patch, vascular closure device, intracardiac septal defect repair device, PFO (patent foramen ovale) closure device, left atrial appendage (LAA) closure device, pericardial patch, myocardial regeneration device, periodontal mesh, anastomosis device, plastic surgery device, breast lift device, mastopexy device, breast reconstruction device, breast augmentation device, breast reduction device, device for breast reconstruction following mastectomy, facial reconstructive device, forehead lift device, brow lift device, eyelid lift device, face lift device, rhytidectomy device, rhinoplasty device, device for malar augmentation, otoplasty device, neck lift device, mentoplasty device, cosmetic repair device, and general surgery devices used to hold back a structure to prevent it from interfering with normal bodily functions such as hemodynamics, peristalsis, and urinary flow, including devices for holding back a malignancy to prevent it interfering with a normal bodily function. A particularly preferred medical device that can be attached to the repositionable fastener is a mastopexy device.

In a preferred embodiment, the medical devices or other implantable components that are attached to one or more fasteners are those that could need to be repositioned after implantation and/or those that are required to be implanted under tension. For example, in the latter case, preferred medical devices include those used in lift procedures, such as mastopexy procedures, face lifts, eyebrow lifts, pelvic floor reconstruction, soft tissue reconstruction, breast reconstruction, and those used as slings. In another embodiment, the medical devices include devices designed for load sharing, including load bearing devices that are responsive to soft tissue reinforcement, and devices where mechanical loading of tissue stimulates the development of tissue, particularly strong tissues that can meet the demands of the local tissue environment.

A particularly preferred medical device that can be attached to the repositionable fastener is a surgical mesh, more preferably a monofilament mesh, and even more preferably a monofilament mesh made from poly-4-hydroxybutyrate.

Other implantable components that can be attached to the repositionable fastener to form the implant include, but are not limited to, non-wovens, films, sponges, foams, three-dimensional shapes, multifilament, monofilament, mesh, molded objects, laminates, electrospun fabrics, dry-spun fabrics, centrifugally spun fabrics, thermoforms, pultruded forms, components with shape memory, and components that can be temporarily deformed and resume their shape unaided.

In another preferred embodiment, a medical device or implantable component that can be attached to the repositionable fastener has one or more of the following properties: a tensile strength greater than 1 MPa, a tensile strength less than 10 GPa, a tensile strength between 1 MPa and less than 10 GPa; a burst strength measured with a ⅜-in ball that is greater than 0.01 lb force, preferably greater than 0.1 lb force, more preferably greater than 1 lb force, and even more preferably greater than 10 lb force; a burst strength measured with a ⅜-in ball that is between 0.01 lb force and 500 lb force; a tensile modulus greater than 1 MPa, a tensile modulus less than 10 GPa, a tensile strength between 1 MPa and less than 10 GPa; an elongation to break less than 1,200%, more preferably less than 500%, and even more preferably less than 100%; an elongation to break between 1% and 1,200%; a suture pull out strength between 0.01 kgf and 250 kgf.

In yet another preferred embodiment the medical device or implantable component when attached to the fastener can withstand a force of at least 10 gram force (gf), more preferably greater than 100 gf, and still more preferably up to 100 kgf when implanted.

In a preferred embodiment, the medical device or other implantable component that is attached to the fastener is absorbable, and in an even more preferred embodiment, both the medical device (or other implantable component) and the fastener are absorbable. In a preferred embodiment, the medical device or other implantable component include one or more of the following polymers, copolymers or blends: polymer, copolymer or blend including one or more of the following monomers: glycolic acid, glycolide, lactic acid, lactide, 1,4-dioxanone, trimethylene carbonate, 3-hydroxybutyric acid, 4-hydroxybutyric acid, or ε-caprolactone; poly (lactides); poly(glycolides); poly(lactide-co-glycolides); poly(lactic acid); poly(glycolic acid); poly(lactic acid-coglycolic acids); polycaprolactones; poly(orthoesters); polyanhydrides; poly(phosphazenes); polyhydroxyalkanoates; poly-3-hydroxybutyrate, poly-4-hydroxybutyrate-co-3-hydroxyvalerate, poly-4-hydroxybutyrate; poly-3-hydroxybutyrate-co-4-hydroxybutyrate; synthetically or biologically prepared polyesters; polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone or combinations thereof. In a particularly preferred embodiment, the medical device or implantable component that is attached to the fastener includes poly-4-hydroxybutyrate or copolymer thereof.

V. Methods of Implanting

The repositionable fasteners may be used in procedures for the repair, replacement or regeneration of hard or soft tissues. In a preferred embodiment the fasteners are used in procedures for the repair, replacement, remodeling, lifting, or regeneration of soft tissues. In a particularly preferred embodiment, the fasteners are used in procedures where it may be necessary to make adjustments to the positions of medical devices and implantable components.

In one embodiment, the fasteners are attached to a medical device or implantable component prior to implantation. However, a medical device or implantable component may be positioned in the body before the fastener is attached, and fixed in tissue.

In a preferred embodiment, the fasteners are used in procedures where temporary support is required, for example, in certain repair, lifting, and remodeling procedures as well as procedures where the tissue may be placed under tension, such as in the approximation of wounds. In a preferred embodiment, the fasteners may be used to approximate tissues in the face, neck and breast, and to elevate these tissues. There are also significant advantages in using the fasteners in minimally invasive procedures, and in open procedures where there is restricted access to the fixation site. For example, the fasteners can be used to easily fixate mesh in a lateral position during a mesh-assisted mastopexy procedure. In a particularly preferred embodiment, the fasteners are attached to surgical meshes, and these implants are used in mesh-assisted mastopexy procedures.

In one embodiment, the fastener may be implanted in tissue and then a medical device or other implantable component attached to the fastener to secure the device or implantable component in place. In this embodiment, the fastener can be implanted by: (i) positioning the side of the fastener with the emanating tissue retainers on a tissue surface, and (ii) moving the fastener in a first direction so that the retainers engage the tissue. If necessary, the fastener can be re-positioned by moving the fastener in a second direction that is opposite to the first direction so that the tissue retainers are removed from the tissue, moving the fastener to a second location, and re-implanting the fastener at a second location. Once the fastener has been located in the desired position, it can be attached to a medical device or other implantable component by one of the methods described above.

In a preferred embodiment, the fastener is attached to a medical device or other implantable component to form an implant prior to implantation. If desired, the implant may include more than one fastener. For example, an implant can be produced by attaching two, three, four, five, six, or more fasteners to a medical device or implantable component. In a preferred embodiment, the medical device or other implantable component is first implanted in its desired location, and then in a second step the one or more fasteners attached to the medical device or implantable component are implanted in tissue to fix the implant in position. In this second step, each fastener is positioned so that the emanating tissue retainers are in contact with the tissue. Each fastener is then moved in a first direction so that the retainers engage the tissue to hold the device or implantable component in place. If necessary, a fastener can be re-positioned by moving the fastener in a second direction that is opposite to the first direction so that the tissue retainers are removed from the tissue, moving the fastener to a second location, and re-implanting the fastener at a second location.

The fasteners may be used to fixate medical devices and implantable components under tension or with no tension. In a particularly preferred embodiment, the fasteners of an implant may be implanted in tissue so that they apply tension to the implant. For example, a surgical mesh with fasteners at opposite ends of the mesh may be implanted so that the fasteners apply tension to the mesh. The amount of tension applied to an implant can be adjusted by varying the position of the fasteners in the tissue. In a preferred embodiment, the fasteners are used to apply tension to tissues in lift procedures.

In another embodiment, an implant may be prepared that includes two or more repositionable fasteners connected to a three-dimensional mesh with shape memory. FIGS. 3A and B show an example of two repositionable fasteners attached to a three-dimensional mesh. This implant may be used for example in a mastopexy procedure, preferably a minimally invasive mastopexy procedure, by implantation into a suitably dissected tissue plane to confer shape to the breast. This implants may, for example, be rolled up into a small cylindrical shape, placed inside a tubular inserter, and implanted through a small incision, such as a standard size incision at the inframammary fold that is usually used for breast augmentation. Once released in vivo, these implants will resume their original three-dimensional shapes, and may be moved into position, for example, to confer shape to the host's breast tissue or an anatomical shape of the breast. In one preferred embodiment, the implant is delivered by employing an IMF incision used as the entry point for dissection, along with a periareolar incision, in a mastopexy procedure. Once skin removal and dissection is complete, a three-dimensional shape memory implant can be deployed in vivo and allowed to resume its preformed three-dimensional shape. The three-dimensional implant may be fixed in place by deploying the repositionable fasteners, and its position or tension adjusted if necessary by repositioning the fasteners. Alternatively, the three dimensional implants can be implanted using traditional open surgery techniques.

The present invention will be further understood by reference to the following non-limiting examples.

Figure 9:
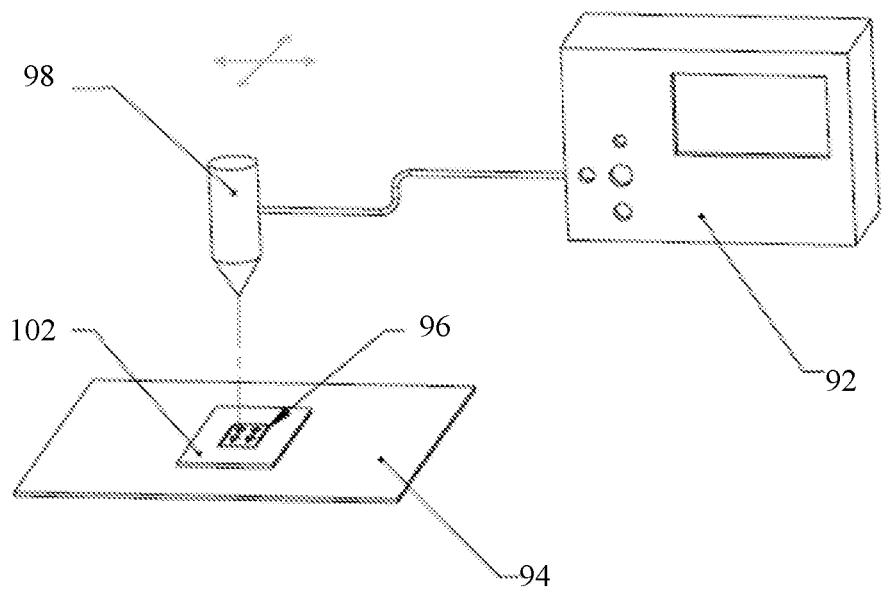
FIG. 9 is a diagram showing the laser cutting setup used to prepare a fastener from a film or sheet. The setup includes a laser control unit (92), a laser head with computer aided XYZ motion (98), a work station (94), a film substrate (102) and a laser cut pattern to form a flexible anchor (96).

Example 1: Manufacture of a Repositionable Fastener with Swivel Anchors by Laser Cutting A thin oriented film made of poly-4-hydroxybutyrate (P4HB) with a uniform thickness of 0.7 mm, was placed on a laser-cutting table (FIG. 9 shows the laser setup). The setup includes a laser control unit (92), a laser head with CAD (computer aided design) XYZ motion (98), a work station (94), a film substrate (102) and a laser cut pattern to form a flexible anchor (96). A $CO_2$ laser source was located above the film, and was used to cut a pre-determined pattern of the perimeter of the repositionable fastener, 30 swivel anchors, and 24 pores (holes) as shown in FIG. 8. To create the pattern of swivel anchors and the perimeter of the fastener, the laser power was set between 40 to 60 watts with a focal distance ranging from 0.5 to 2.0 cm. Once cutting was complete, the cut shape of film was separated from the excess film material, and placed onto an angle plate consisting of a metal base plate with orientation pins.

An example of a section of a suitable metal base plate with orientation pins that can be used to set the angle of the anchors is shown in FIG. 10. The set up includes a base plate (206), orientation needles (204) set at the desired angle from the plate (206) and a supportive backing with cut anchors (202). The orientation pins were press-fit to the base plate at a constant angle of 45°. A total of 30 orientation pins were press-fit to the plate to equal the number of laser cut swivel anchors, and the pins were offset so that the pins lined up directly with the top half of the pre-cut swivel anchors. The flat laser cut shape was then manually driven through the pins (as illustrated in FIG. 10). As the pins pierced through the laser cut film shape, the anchors separated from the film and rotated to match the angle of the pins on the base plate. The assembly of the pin plate and attached film was then submerged in a hot water bath at 57° C. for 10-20 seconds and was then immediately transferred to a cold-water bath ($\leq 18°$ C.) for a minimum of 10 min to allow for quenching. The repositionable fastener with heat-set swivel anchors set to the desired angle was then removed from the cold-water bath, and left to air-dry. The resulting repositionable fastener is shown in FIG. 2.

Example 2: Manufacture of a Repositionable Fastener with Swivel Anchors by Die Cutting A thin oriented film made of poly-4-hydroxybutyrate (P4HB) of uniform thickness (ranging from 0.5 to 1.0 mm) was cut to produce the anchor pattern shown in FIG. 2 by pressing a custom steel rule die onto the P4HB film instead of using a laser to cut the film as described in Example 1. The subsequent steps described in Example 1 wherein the swivel anchors were produced from the cut film with the metal base plate and using orientation pins as illustrated in FIG. 10 was used to produce the heat-set repositionable fastener with swivel anchors.

Example 3: Manufacture of a Repositionable Fastener with Swivel Anchors by Injection Molding A two-part mold with mating cavities was machined to generate the pattern shown in FIG. 1. Molten poly-4-hydroxybutyrate (P4HB) was injected through an injection port (gate) into the mold with a pressure of 4-6 tons to fill out the cavity formed by the assembled top and bottom halves of the mold, and was continued until excess polymer flowed out of the relief ports. The mold was allowed to cool to room temperature, disassembled, and the repositionable fastener removed from the mold. Excess polymer was trimmed form the molded fastener. An illustration of a two-part mold that can be used to produce a fastener with 4 swivel anchors is shown in FIG. 11.

Example 4: Attachment of the Repositionable Fastener to a Mesh by Fusion (Heat Welding)

A repositionable fastener (with dimensions of 20 mm×30 mm) made from poly-4-hydroxybutyrate (as described above) was fused to a monofilament mesh also made of poly-4-hydroxybutyate by placing the fastener and mesh in a "latch weld" type configuration as illustrated in FIG. 12. FIG. 12 shows oriented swivel anchors (402), a supportive backing (404), an electric or fluid supply depending on sealer type (406), alignment pins (408a, 408b) to apply uniform pressure during sealing, a heat setter (502), set at 57-60° C. (for processing P4HB, for example), and a substrate (504) to attach supportive backing (404) onto. The overlapping area of the latch weld was placed between two heated plates with a thermos-couple to control the surface temperature of the plates. The width of the heated plates ranged from 4-10 mm (weld width) and the length of the plates ranged from 30-75 mm. The top plate was moved vertically along two shafts to apply pressure (5-10 psi) and heat (55-65° C.) for 2-3 min in order to fuse the fastener to the mesh. Once the welding was completed, and without relieving pressure, the heating element was turned off, and the assembly (fastener, mesh and heat welder) was submerged in a cold-water bath to quench the fused implant for a minimum of 10 min. After 10 min, the welder was disengaged to relieve pressure, and the implant including the fastener fused to the mesh removed from the assembly.

Example 5: Attachment of the Repositionable Fastener to a Three-Dimensional Mesh by Fusion (Heat Welding)

A three-dimensional mesh was attached to two repositionable fasteners by fusion using essentially the same procedure described in Example 4, except the mesh was a three-dimensional mesh with protruding mesh tabs that were used for the fixation. The procedure produced the implant shown in FIGS. 3A and B wherein the with repositionable fasteners (20a and 20b) fused to the mesh tabs (22a and 22b) attached to the three-dimensional mesh (23).

Example 6: Attachment of the Repositionable Fastener to a Mesh Using a Buckle A repositionable fastener incorporating a buckle for attachment to a mesh was produced by laser cutting. The buckle was made with two parallel saw edges through which the mesh was driven to attach the fastener to the mesh as shown in FIG. 6.

Example 7: Attachment of the Repositionable Fastener to a Mesh Using a Clasp A repositionable fastener incorporating a clasp with pins and locking holes as shown in FIGS. 7A and 7B were produced by laser cutting. The mesh was placed over the locking holes of the clasp, and the pins were driven through the mesh pores into their respective mating holes locking the mesh to the repositionable fastener to form an implant.

Modifications and variations of the methods and compositions will be apparent from the foregoing detailed description and are intended to come within the scope of the appended claims.

We claim:

1. An implantable fastener for attachment of a medical device or implantable component to tissue comprising a plurality of tissue retainers emanating from a supportive backing,
   wherein the tissue retainers comprise two tips, and are configured to swivel from a plane of the supportive backing to engage tissue,
   wherein a tip of the tissue retainer projects from each side of the plane of the supportive backing, and
   wherein the fastener is attached to a medical device.

2. The fastener of claim 1 wherein the tissue is soft tissue.

3. The fastener of claim 1 wherein the tissue is hard tissue.

4. The fastener of claim 1 wherein the fastener is absorbable.

5. The fastener of claim 4 wherein the fastener is made from one or more absorbable polymers, copolymers, or blends thereof.

6. The fastener of claim 1 wherein the fastener can be fixed in a first position, removed from that position, and repositioned in a second position different from the first position.

7. The fastener of claim 6 wherein the fastener is fixed in the first position by movement in a first direction and removed when pulled in a direction opposite to the first direction.

8. The fastener of claim 1 wherein the fastener can hold between a 10 gram force (gf) and a 35 kg force (kgf) when implanted in the tissue.

9. The fastener of claim 1 wherein the fastener is attached to the medical device by one or more of the following: locking device, clasp, buckle, latch, clip, pin, stitch, glue, or fusing of the fastener to the medical device.

10. The fastener of claim 1, wherein the fastener is porous.

11. The fastener of claim 1 wherein one or more of the tissue retainers can penetrate the tissue to a depth between 0.01 mm and 10 mm.

12. The fastener of claim 1 wherein the tissue retainers are one or more of the following: barbs, hooks, projections, darts, extensions, bulges, anchors, protuberances, spurs, bumps, points, arrows, spikes, spurs, pointed, jagged, tapered, serrated, sharp edge shaped, wedged-shaped, thorn-shaped, shield-shaped, V-shaped, W-shaped, cogs, and multi-tip.

13. The fastener of claim 1 wherein the tissue retainers are configured to engage the tissue at an angle between 5° and 60° from the plane of the supportive backing.

14. The fastener of claim 1 wherein the length of the tissue retainers, measured from the plane of the supportive backing to a tip of the tissue retainers that pierces the tissue, is between 0.01 mm and 10 mm.

15. The fastener of claim 1 wherein the tissue retainers are oriented in the same direction.

16. The fastener of claim 1 wherein the tissue retainers are positioned in an ordered manner, random manner, spiral manner, patterned manner or staggered manner.

17. The fastener of claim 1 wherein there are between 2 and 1,000 tissue retainers emanating from the supportive backing.

18. The fastener of claim 17 wherein the fastener can hold between a 10 gram force (gf) and a 35 kg force (kgf) when implanted in tissue.

19. The fastener of claim 1 wherein the distance between the tissue retainers is between 50 μm and 2.5 cm.

20. The fastener of claim 1 wherein the supportive backing has a thickness of between 100 μm and 5 mm, or a thickness that varies between 100 μm and 5 mm.

21. The fastener of claim 1 wherein the tissue retainers have a thickness between 100 μm and 5 mm, or a thickness that varies between 100 μm and 5 mm.

22. The fastener of claim 1 wherein the supportive backing has one or more of the following properties: (i) tensile strength between 1 MPa and 10 GPa, (ii) tensile modulus between 1 MPa and 6 GPa, and (iii) elongation to break between 1 and 1,200%.

23. The fastener of claim 1 wherein the supportive backing is a film or sheet.

24. The fastener of claim 5 wherein the polymers, copolymers, or blends thereof comprise one or more of the following monomers: glycolic acid, glycolide, lactic acid, lactide, 1,4-dioxanone, trimethylene carbonate, 3-hydroxybutyric acid, 4-hydroxybutyric acid, or ε-caprolactone.

25. The fastener of claim 5 wherein the polymers, copolymers, or blends thereof are selected from the group consisting of: poly(lactides); poly(glycolides); poly(lactide-co-glycolides); poly(lactic acid); poly(glycolic acid); poly (lactic acid-co-glycolic acids); polycaprolactones; poly (orthoesters); polyanhydrides; poly(phosphazenes); polyhydroxyalkanoates; poly-3-hydroxybutyrate, poly-4-hydroxybutyrate-co-3-hydroxyvalerate, poly-4-hydroxybutyrate; poly-3-hydroxybutyrate-co-4-hydroxybutyrate; synthetically or biologically prepared polyesters; polycarbonates; tyrosine polycarbonates; synthetic polyamides; natural polyamides; polypeptides; poly(amino acids); polyesteramides; poly(dioxanones); poly(alkylene alkylates); polyethers; polyethylene glycol (PEG); polyethylene oxide (PEO); polyvinyl pyrrolidones (PVP); polyurethanes; polyetheresters; polyacetals; polycyanoacrylates; poly(oxyethylene)/poly(oxypropylene) copolymers; polyacetals, polyketals; polyphosphates; phosphorous-containing polymers; polyphosphoesters; polyalkylene oxalates; polyalkylene succinates; poly(maleic acids); chitin; chitosan; modified chitosan; biocompatible polysaccharides; block copolymers of PEG or PVP with one or more polymers selected from the group consisting of poly(lactide), poly (lactide-co-glycolide), and polycaprolcatone; and copolymers or blends thereof.

26. An implant comprising the fastener of claim 1 wherein the fastener is attached to one or more of the following medical devices: monofilament mesh, multifilament mesh, patch, monofilament fiber, multifilament fiber, braid, flat braid, circular braid, ligature, suture, knitted mesh, woven mesh, knitted tubes, wound healing device, bandage, wound dressing, skin substitute, hemostat, organ salvage device, device for soft tissue reinforcement, dural substitute, dural patch, hernia repair device, hernia mesh, hernia plug, device to surgically alter or tighten the lower esophageal sphincter (LES) in order to prevent backflow in the treatment of gastro esophageal reflux disease (GERD), device for temporary wound or tissue support, tissue scaffold, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of stress incontinence, bladder repair device, sphincter muscle repair device, ligament repair device, ligament augmentation device, ligament graft, anterior cruciate ligament repair device, tendon repair device, device for Achilles tendon repair as adjunct reinforcement, tendon graft, tendon augmentation device, rotator cuff repair device, device for Tommy John's repair/ulnar ligament graft reinforcement, device for reinforcement in knee procedures including the reinforcement of anterior, posterior and medial cruciate ligaments, meniscus repair device, meniscus regeneration device, articular cartilage repair device, cardiovascular patch, vascular closure device, intracardiac septal defect repair device, PFO (patent foramen ovale) closure device, left atrial appendage (LAA) closure device, pericardial patch, myocardial regeneration device, periodontal mesh, anastomosis device, plastic surgery device, breast lift device, mastopexy device, breast reconstruction device, breast augmentation device, breast reduction device, device for breast reconstruction following mastectomy, facial reconstructive device, forehead lift device, brow lift device, eyelid lift device, face lift device, rhytidectomy device, rhinoplasty device, device for malar augmentation, otoplasty device, neck lift device, mentoplasty device, cosmetic repair device, and general surgery devices used to hold back a structure to prevent it from interfering with normal bodily functions.

27. The implant of claim 26 wherein the medical device is a mastopexy device, and wherein the mastopexy device comprises a monofilament knitted mesh.

28. The implant of claim 27 wherein the location of the mastopexy device in the patient can be adjusted after initial implantation from a first position, and repositioned in a second position different from the first position by removing the fastener from the first position and implanting it at the second position.

29. The implant of claim 27 wherein the implant comprises poly-4-hydroxybutyrate or a copolymer thereof.

30. The implant of claim 27 wherein the monofilament knitted mesh is fused, buckled, latched, clipped, pinned, stitched, or glued to the fastener.

31. The implant of claim 26 further comprising an additive or bioactive agent.

32. The implant of claim 31 wherein the tissue retainers comprise an additive or bioactive agent.

33. The implant of claim 31 wherein the additive or bioactive agent is a nucleant, plasticizer, imaging agent, radioactive marker, antimicrobial agent, small-molecule drug, anti-inflammatory agent, immunomodulatory agent, molecule that promotes cell migration, molecule that promotes or retards cell division, molecule that promotes or retards cell proliferation and differentiation, molecule that stimulates phenotypic modification of cells, molecule that promotes or retards angiogenesis, molecule that promotes or retards vascularization, molecule that promotes or retards extracellular matrix disposition, signaling ligand, platelet rich plasma, peptide, protein, glycoprotein, anesthetic, hormone, antibody, growth factor, fibronectin, laminin, vitronectin, integrin, steroid, hydroxyapatite, silver particle, vitamin, non-steroidal anti-inflammatory drug, chitosan and derivatives thereof, alginate and derivatives thereof, collagen, sugar, polysaccharide, nucleotide, oligonucleotide, lipid, lipoprotein, hyaluronic acid or a derivative thereof, allograft material, xenograft material, ceramic, resorbable ceramic, nucleic acid molecule, antisense molecule, aptamer, siRNA, nucleic acid, or a combination thereof.

34. The implant of claim 33 wherein the antimicrobial agent is rifampin, minocycline, or a salt thereof.

35. A method for preparing the fastener of claim 1 comprising forming the supportive backing with the tissue retainers from a film or sheet, wherein the tissue retainers are formed in the film or sheet by mechanical cutting, machining, laser cutting, stamping, or punching, or forming the supportive backing with the tissue retainers by molding.

36. The fastener of claim 8 wherein the fastener can hold a force between a 10 gf and a 25 kgf when implanted in the tissue.

37. The fastener of claim 36 wherein the fastener can hold a force between a 1 kgf and a 10 kgf when implanted in the tissue.

38. The fastener of claim 11 wherein one or more of the tissue retainers can penetrate the tissue to a depth between 1 mm and 6 mm.

39. The fastener of claim 38 wherein one or more of the tissue retainers can penetrate the tissue to a depth between 2 mm and 5 mm.

40. The fastener of claim 13 wherein the tissue retainers are configured to engage the tissue at an angle between 15° and 45° from the plane of the supportive backing.

41. The fastener of claim 14 wherein the length of the tissue retainers, measured from the plane of the supportive backing to the tip of the tissue retainers that pierces the tissue, is between 0.25 mm and 5 mm.

42. The fastener of claim 19 wherein the distance between the tissue retainers is between 0.5 mm and 5 mm.

43. The implant of claim 27 wherein the mastopexy device comprises an oriented monofilament knitted mesh.

* * * * *

UNITED STATES PATENT AND TRADEMARK OFFICE
CERTIFICATE OF CORRECTION

| | | |
|---|---|---|
| PATENT NO. | : 10,507,020 B2 | Page 1 of 1 |
| APPLICATION NO. | : 15/292592 | |
| DATED | : December 17, 2019 | |
| INVENTOR(S) | : Skander Limem, Bruce Van Natta and Kevin Cristadoro | |

It is certified that error appears in the above-identified patent and that said Letters Patent is hereby corrected as shown below:

In the Specification
Column 3, Line 34, replace "a method of is a method of fixating" with --a method of fixating--.
Column 3, Lines 58-59, replace "showing an implantable" with --showing implantable--.
Column 4, Line 26, replace "the clasp (61), which includes" with --the clasp, which includes--.
Column 4, Line 59, replace "to the supportive backing" with --to attach supportive backing--.
Column 9, Line 47, replace "25 tissue retainers" with --32 tissue retainers--.
Column 11, Line 65, replace "poly(lactide-co-glycolide, or polycaprolcatone" with --poly (lactide-co-glycolide), or polycaprolactone--.
Column 12, Lines 66-67, replace "tetrahydofurfuryl oleate" with --tetrahydrofurfuryl oleate--.
Column 16, Line 53, replace "30 tissue retainers, and 24 pores" with --25 tissue retainers, and 15 pores--.
Column 18, Line 40, replace "is shown in FIG. 6" with --is shown in FIG. 6A--.
Column 18, Line 40, replace "FIG. 6 shows" with --FIG. 6A shows--.
Column 18, Line 42, replace "repositionable fastener (52) using using an adjustable buckle (51)" with --repositionable fastener (500) using an adjustable buckle (50)--.
Column 18, Line 46, replace "from FIG. 6, that the buckle (51)" with --from FIGs. 6A and 6B, that the buckle (50)--.
Column 21, Lines 22-23, replace "poly(lactide-co-glycolide, or polycaprolcatone" with --poly (lactide-co-glycolide), or polycaprolactone--.
Column 22, Line 48, replace "implants may" with --implant may--.
Column 23, Lines 15-16, replace "30 swivel anchors, and 24 pores" with --25 swivel anchors, and 15 pores--.
Column 23, Line 29, replace "30 orientation pins" with --25 orientation pins--.
Column 23, Line 44, replace "FIG. 2." with --FIG. 8.--.

In the Claims
Claim 25, Column 26, Line 47, replace "polycaprolcatone" with --polycaprolactone--.
Claim 33, Column 28, Line 6, replace "extracellular matrix disposition" with --extracellular matrix deposition--.

Signed and Sealed this
Nineteenth Day of May, 2020

Andrei Iancu
*Director of the United States Patent and Trademark Office*